US008950405B2

(12) United States Patent
Grenon et al.

(10) Patent No.: US 8,950,405 B2
(45) Date of Patent: *Feb. 10, 2015

(54) TREATMENT OF OBSTRUCTIVE DISORDERS OF THE EYE OR EYELID

(75) Inventors: Stephen M. Grenon, Durham, NC (US);
Donald R. Korb, Boston, MA (US);
Timothy R. Willis, Raleigh, NC (US)

(73) Assignee: TearScience, Inc., Morrisville, NC (US)

( * ) Notice: Subject to any disclaimer, the term of this patent is extended or adjusted under 35 U.S.C. 154(b) by 1424 days.

This patent is subject to a terminal disclaimer.

(21) Appl. No.: 11/928,681

(22) Filed: Oct. 30, 2007

(65) Prior Publication Data

US 2008/0046048 A1    Feb. 21, 2008

Related U.S. Application Data

(63) Continuation-in-part of application No. 11/541,418, filed on Sep. 29, 2006, now Pat. No. 7,981,145, and a continuation-in-part of application No. 11/434,054, filed on May 15, 2006, now Pat. No. 8,083,787, and a (Continued)

(51) Int. Cl.
*A61F 7/00*    (2006.01)
*A61F 7/02*    (2006.01)
*A61F 9/007*    (2006.01)

(52) U.S. Cl.
CPC .............. *A61F 7/02* (2013.01); *A61F 9/00772* (2013.01); *A61F 2007/0004* (2013.01); *A61F 2007/0261* (2013.01)
USPC ......................................................... 128/898

(58) Field of Classification Search
USPC ............................................ 128/898; 607/96
See application file for complete search history.

(56) References Cited

U.S. PATENT DOCUMENTS

| 1,006,945 A | 10/1911 | Houston |
| 1,924,315 A | 8/1933 | Hemphill et al. |

(Continued)

FOREIGN PATENT DOCUMENTS

| AU | 2011203832 A1 | 8/2012 |
| AU | 2011302478 A1 | 3/2013 |

(Continued)

OTHER PUBLICATIONS

Sullivan, Benjamin D., et al., "Impact of Antiandrogen Treatment on the Fatty Acid Profile of Neutral Lipids in Human Meibomian Gland Secretions," The Journal of Clinical Endocrinology & Metabolism, vol. 85, No. 12, 2000, 8 pages (pp. 4866-4873).

(Continued)

*Primary Examiner* — Aaron Roane
(74) *Attorney, Agent, or Firm* — Withrow & Terranova PLLC

(57) ABSTRACT

In accordance with certain illustrative embodiments, methods and apparatuses of treating obstructive disorders of the structure of an eye or eyelid are disclosed. The treating may involve applying heat to the structure containing the obstructive disorder to melt an obstruction in the structure and place the obstruction in a melted state. The heat may be maintained for a time period to melt the obstruction and place the obstruction in the melted state. The structure may be treated by expressing the melted obstruction from the structure. The treating may be carried out either during the time period or after the time period when heat is applied but while the obstruction is in the melted state. In certain embodiments, the method further involves subsequently treating the structure by use of a pharmacological agent. This abstract is not to be considered limiting, since other embodiments may deviate from the features described in this abstract.

29 Claims, 3 Drawing Sheets

Related U.S. Application Data continuation-in-part of application No. 11/434,033, filed on May 15, 2006, and a continuation-in-part of application No. 11/434,446, filed on May 15, 2006, now abandoned, and a continuation-in-part of application No. 11/541,308, filed on Sep. 29, 2006, and a continuation-in-part of application No. 11/541,291, filed on Sep. 29, 2006, now Pat. No. 7,981,095.

(56) References Cited

U.S. PATENT DOCUMENTS

| | | |
|---|---|---|
| 2,545,724 A | 3/1951 | Curtis |
| 2,891,252 A | 6/1959 | Lazo |
| 3,140,390 A | 7/1964 | Smith et al. |
| 3,173,419 A | 3/1965 | Dubilier et al. |
| 3,333,586 A | 8/1967 | Bellis et al. |
| 3,404,678 A | 10/1968 | Von Ardenne |
| 3,415,299 A | 12/1968 | Hinman, Jr. et al. |
| 3,667,476 A | 6/1972 | Muller |
| 3,952,735 A | 4/1976 | Wirtschafter et al. |
| 4,069,084 A | 1/1978 | Mlodozeniec et al. |
| 4,131,115 A | 12/1978 | Peng |
| 4,261,364 A | 4/1981 | Haddad et al. |
| 4,387,707 A | 6/1983 | Polikoff |
| 4,778,457 A | 10/1988 | York |
| 4,883,454 A | 11/1989 | Hamburg |
| 4,914,088 A | 4/1990 | Glonek et al. |
| 4,918,818 A | 4/1990 | Hsieh |
| 4,955,377 A | 9/1990 | Lennox et al. |
| 4,958,632 A | 9/1990 | Duggan |
| 5,030,214 A | 7/1991 | Spector |
| 5,097,829 A | 3/1992 | Quisenberry |
| 5,151,100 A | 9/1992 | Abele et al. |
| 5,158,082 A | 10/1992 | Jones |
| 5,169,384 A | 12/1992 | Bosniak et al. |
| 5,213,097 A | 5/1993 | Zeindler |
| 5,251,627 A | 10/1993 | Morris |
| 5,283,063 A | 2/1994 | Freeman |
| 5,314,456 A | 5/1994 | Cohen |
| 5,327,886 A | 7/1994 | Chiu |
| 5,343,561 A | 9/1994 | Adamo |
| D352,106 S | 11/1994 | Fanney et al. |
| 5,368,582 A | 11/1994 | Bertera |
| 5,368,591 A | 11/1994 | Lennox et al. |
| 5,377,701 A | 1/1995 | Fang |
| 5,419,772 A | 5/1995 | Teitz et al. |
| 5,425,380 A | 6/1995 | Hudson et al. |
| 5,496,311 A | 3/1996 | Abele et al. |
| 5,601,548 A | 2/1997 | Smith et al. |
| 5,628,772 A | 5/1997 | Russell |
| 5,643,336 A | 7/1997 | Lopez-Claros |
| 5,700,238 A | 12/1997 | Hyson |
| 5,720,773 A | 2/1998 | Lopez-Claros |
| 5,769,806 A | 6/1998 | Radow |
| 5,782,857 A | 7/1998 | Machuron |
| 5,807,357 A | 9/1998 | Kang |
| 5,836,927 A | 11/1998 | Fried |
| 5,893,719 A * | 4/1999 | Radow .................. 434/271 |
| 5,958,912 A | 9/1999 | Sullivan |
| 5,960,608 A | 10/1999 | Ohtonen |
| 5,964,723 A | 10/1999 | Augustine |
| 6,007,501 A | 12/1999 | Cabados et al. |
| 6,024,095 A | 2/2000 | Stanley, III |
| 6,090,060 A | 7/2000 | Radow |
| 6,107,289 A | 8/2000 | Sullivan |
| 6,110,292 A | 8/2000 | Jewett et al. |
| 6,112,900 A | 9/2000 | Adkins, Jr. |
| 6,113,561 A | 9/2000 | Augustine |
| 6,153,607 A | 11/2000 | Pflugfelder et al. |
| 6,155,995 A * | 12/2000 | Lin ......................... 601/15 |
| 6,181,970 B1 | 1/2001 | Kasevich |
| 6,193,740 B1 | 2/2001 | Rodriguez |
| 6,206,842 B1 | 3/2001 | Tu et al. |
| 6,213,966 B1 | 4/2001 | Augustine |
| 6,273,886 B1 | 8/2001 | Edwards et al. |
| 6,275,735 B1 | 8/2001 | Jarding et al. |
| 6,309,364 B1 | 10/2001 | Cathaud et al. |
| 6,312,397 B1 | 11/2001 | Gebhard |
| D456,079 S | 4/2002 | Fujii |
| 6,423,018 B1 | 7/2002 | Augustine |
| 6,425,888 B1 | 7/2002 | Embleton et al. |
| 6,438,398 B1 | 8/2002 | Pflugfelder et al. |
| 6,455,583 B1 | 9/2002 | Pflugfelder et al. |
| 6,482,203 B2 | 11/2002 | Paddock et al. |
| 6,490,488 B1 | 12/2002 | Rudie et al. |
| D472,637 S | 4/2003 | Cooper et al. |
| 6,544,257 B2 | 4/2003 | Nagase et al. |
| D477,084 S | 7/2003 | Menezes et al. |
| 6,641,264 B1 | 11/2003 | Schwebel |
| 6,648,904 B2 | 11/2003 | Altshuler et al. |
| 6,706,001 B2 | 3/2004 | Fresco |
| 6,780,176 B2 | 8/2004 | Hasegawa |
| 6,788,977 B2 | 9/2004 | Fenn et al. |
| 6,827,898 B1 | 12/2004 | Fausset et al. |
| 6,840,954 B2 | 1/2005 | Dietz et al. |
| 6,860,852 B2 | 3/2005 | Schonenberger et al. |
| 6,860,880 B2 | 3/2005 | Treat et al. |
| 6,874,884 B2 | 4/2005 | Schwebel |
| 6,882,885 B2 | 4/2005 | Levy, Jr. et al. |
| 6,886,933 B2 | 5/2005 | Schwebel |
| 6,908,195 B2 | 6/2005 | Fuller |
| 6,925,317 B1 | 8/2005 | Samuels et al. |
| 6,974,454 B2 | 12/2005 | Hooven |
| 7,001,379 B2 | 2/2006 | Behl et al. |
| 7,004,942 B2 | 2/2006 | Laird et al. |
| 7,036,928 B2 | 5/2006 | Schwebel |
| 7,069,084 B2 | 6/2006 | Yee |
| 7,108,694 B2 | 9/2006 | Miura et al. |
| 7,118,591 B2 | 10/2006 | Frank et al. |
| 7,122,013 B2 | 10/2006 | Liu |
| 7,122,047 B2 | 10/2006 | Grahn et al. |
| 7,123,968 B1 | 10/2006 | Casscells, III et al. |
| 7,211,070 B2 * | 5/2007 | Soroudi ..................... 604/294 |
| 7,229,468 B2 | 6/2007 | Wong et al. |
| 7,231,922 B2 | 6/2007 | Davison et al. |
| D546,459 S | 7/2007 | Banryu |
| D552,736 S | 10/2007 | Yamaoka |
| D553,750 S | 10/2007 | Yamaoka |
| 7,316,657 B2 | 1/2008 | Kleinhenz et al. |
| 7,357,500 B2 | 4/2008 | Schwebel |
| 7,384,405 B2 | 6/2008 | Rhoades |
| 7,442,174 B2 | 10/2008 | Butler |
| 7,513,893 B2 | 4/2009 | Soroudi |
| 7,559,907 B2 | 7/2009 | Krempel et al. |
| 7,594,728 B2 | 9/2009 | Seal et al. |
| 7,637,878 B2 | 12/2009 | Lin |
| D612,941 S | 3/2010 | Youngquist et al. |
| D614,774 S | 4/2010 | Gausmann et al. |
| 7,712,899 B2 | 5/2010 | Tanassi et al. |
| 7,976,573 B2 | 7/2011 | Korb et al. |
| D645,565 S | 9/2011 | Smith et al. |
| 8,025,689 B2 | 9/2011 | Korb et al. |
| 8,128,673 B2 | 3/2012 | Korb et al. |
| 8,128,674 B2 | 3/2012 | Korb et al. |
| 8,137,390 B2 | 3/2012 | Korb et al. |
| 8,187,311 B2 | 5/2012 | Korb et al. |
| 8,262,715 B2 | 9/2012 | Wong, Jr. et al. |
| 8,455,016 B2 | 6/2013 | Maskin |
| 8,617,229 B2 | 12/2013 | Korb et al. |
| 8,628,504 B2 | 1/2014 | Grenon et al. |
| 8,791,158 B2 | 7/2014 | Dalton et al. |
| 2001/0039442 A1 | 11/2001 | Gorge et al. |
| 2001/0041886 A1 | 11/2001 | Durkin et al. |
| 2002/0035345 A1 | 3/2002 | Beck |
| 2002/0099094 A1 | 7/2002 | Anderson |
| 2002/0111608 A1 | 8/2002 | Baerveldt et al. |
| 2002/0128696 A1 | 9/2002 | Pearl et al. |
| 2002/0156402 A1 | 10/2002 | Woog et al. |
| 2003/0050594 A1 | 3/2003 | Zamierowski |
| 2003/0056281 A1 | 3/2003 | Hasegawa |
| 2003/0065277 A1 | 4/2003 | Covington |
| 2003/0073987 A1 | 4/2003 | Sakurai et al. |
| 2003/0100936 A1 | 5/2003 | Altshuler et al. |

(56) References Cited

U.S. PATENT DOCUMENTS

| | | |
|---|---|---|
| 2003/0114426 A1 | 6/2003 | Pflugfelder et al. |
| 2003/0139790 A1 | 7/2003 | Ingle et al. |
| 2003/0195438 A1 | 10/2003 | Petillo |
| 2003/0211043 A1 | 11/2003 | Korb |
| 2003/0233135 A1* | 12/2003 | Yee .................. 607/48 |
| 2004/0064169 A1 | 4/2004 | Briscoe et al. |
| 2004/0064171 A1 | 4/2004 | Briscoe et al. |
| 2004/0076695 A1 | 4/2004 | Gilbard |
| 2004/0111138 A1 | 6/2004 | Bleam et al. |
| 2004/0153093 A1 | 8/2004 | Donovan |
| 2004/0199158 A1 | 10/2004 | Hood et al. |
| 2004/0237969 A1* | 12/2004 | Fuller .................... 128/858 |
| 2004/0249427 A1 | 12/2004 | Nabilsi |
| 2004/0260209 A1 | 12/2004 | Ella et al. |
| 2005/0022823 A1 | 2/2005 | Davison et al. |
| 2005/0119629 A1 | 6/2005 | Soroudi |
| 2005/0143798 A1 | 6/2005 | Bleam et al. |
| 2005/0187502 A1 | 8/2005 | Krempel et al. |
| 2005/0220742 A1 | 10/2005 | Breen |
| 2005/0234506 A1 | 10/2005 | Weser |
| 2006/0018953 A1 | 1/2006 | Guillon et al. |
| 2006/0030604 A1 | 2/2006 | Elsinger et al. |
| 2006/0055878 A1 | 3/2006 | Yee |
| 2006/0069420 A1 | 3/2006 | Rademacher et al. |
| 2006/0104914 A1 | 5/2006 | Soroudi |
| 2006/0135890 A1 | 6/2006 | Tsai |
| 2006/0136022 A1 | 6/2006 | Wong, Jr. et al. |
| 2006/0139569 A1 | 6/2006 | Schwebel |
| 2006/0154901 A1 | 7/2006 | Pflugfelder et al. |
| 2006/0157064 A1 | 7/2006 | Davison et al. |
| 2006/0183698 A1 | 8/2006 | Abelson |
| 2006/0212101 A1 | 9/2006 | Cheng |
| 2006/0233859 A1 | 10/2006 | Whitcup et al. |
| 2007/0016256 A1 | 1/2007 | Korb et al. |
| 2007/0027411 A1 | 2/2007 | Ella et al. |
| 2007/0049913 A1 | 3/2007 | Grenon et al. |
| 2007/0173799 A1 | 7/2007 | Hsia |
| 2007/0203462 A1 | 8/2007 | Soroudi |
| 2007/0270760 A1 | 11/2007 | Dacquay et al. |
| 2007/0280924 A1 | 12/2007 | Daniels et al. |
| 2007/0282282 A1 | 12/2007 | Wong et al. |
| 2008/0051741 A1 | 2/2008 | Grenon et al. |
| 2008/0075787 A1 | 3/2008 | Hibino |
| 2008/0132973 A1 | 6/2008 | Lord et al. |
| 2008/0200848 A1 | 8/2008 | Avni |
| 2009/0043365 A1 | 2/2009 | Friedland et al. |
| 2009/0137533 A1 | 5/2009 | Adkins, Jr. |
| 2009/0192478 A1 | 7/2009 | Soroudi |
| 2009/0306111 A1 | 12/2009 | Nakamura et al. |
| 2009/0306607 A1 | 12/2009 | Yasuhiro |
| 2010/0100029 A1 | 4/2010 | Maskin |
| 2010/0292630 A1 | 11/2010 | Maskin |
| 2011/0039805 A1 | 2/2011 | Pflugfelder et al. |
| 2011/0059902 A1 | 3/2011 | Sullivan et al. |
| 2011/0059925 A1 | 3/2011 | Donnenfeld |
| 2011/0124725 A1 | 5/2011 | Maskin |
| 2011/0172302 A1 | 7/2011 | Dalton et al. |
| 2011/0203832 A1 | 8/2011 | Schrock |
| 2011/0251532 A1 | 10/2011 | Yang |
| 2011/0273550 A1 | 11/2011 | Amano et al. |
| 2011/0294897 A1 | 12/2011 | Aberg et al. |
| 2012/0003296 A1 | 1/2012 | Shantha et al. |
| 2012/0065556 A1 | 3/2012 | Smith et al. |
| 2012/0093876 A1 | 4/2012 | Ousler, III et al. |
| 2012/0109041 A1 | 5/2012 | Munz |
| 2012/0128763 A1 | 5/2012 | Maskin |
| 2012/0209154 A1 | 8/2012 | Williams, III et al. |
| 2012/0220612 A1 | 8/2012 | Nakamura et al. |
| 2012/0321673 A1 | 12/2012 | Ogawa et al. |
| 2013/0045927 A1 | 2/2013 | Dana et al. |
| 2013/0046367 A1 | 2/2013 | Chen |
| 2013/0053733 A1 | 2/2013 | Korb et al. |
| 2013/0065867 A1 | 3/2013 | Smith et al. |
| 2013/0110101 A1 | 5/2013 | Van Valen et al. |
| 2013/0131171 A1 | 5/2013 | Maskin |
| 2013/0172790 A1 | 7/2013 | Badawi |
| 2013/0172829 A1 | 7/2013 | Badawi |

FOREIGN PATENT DOCUMENTS

| | | |
|---|---|---|
| CA | 2331257 A1 | 11/1999 |
| CA | 2679448 A1 | 9/2008 |
| CA | 2787114 A1 | 7/2011 |
| CA | 2809274 A1 | 3/2012 |
| CN | 2650737 Y | 10/2004 |
| CN | 1631344 A | 6/2005 |
| CN | 2855388 Y | 1/2007 |
| CN | 102204854 A | 10/2011 |
| CN | 101663064 B | 3/2013 |
| CN | 103002737 A | 3/2013 |
| CN | 102600008 B | 5/2014 |
| DE | 202005011496 U1 | 7/2006 |
| EP | 1816980 A2 | 8/2007 |
| EP | 2151438 A1 | 2/2010 |
| EP | 1587468 B1 | 1/2011 |
| EP | 2523556 A1 | 11/2012 |
| JP | 0370557 A | 3/1991 |
| JP | 06269473 | 9/1994 |
| JP | 06315499 A | 11/1994 |
| JP | 10085248 A | 4/1998 |
| JP | 11221247 | 8/1999 |
| JP | 2000225141 A | 8/2000 |
| JP | 2001276113 A | 10/2001 |
| JP | 200278727 | 3/2002 |
| JP | 2004350803 A | 12/2004 |
| JP | 2005237724 A | 9/2005 |
| JP | 2006198249 | 8/2006 |
| JP | 2006198249 A | 8/2006 |
| JP | U3112008 B | 7/2008 |
| JP | 2010155012 A | 7/2010 |
| KR | 20120115380 A | 10/2012 |
| MX | 2012008110 A | 10/2012 |
| WO | 9810723 A1 | 3/1998 |
| WO | 99/09965 | 3/1999 |
| WO | 9920213 A1 | 4/1999 |
| WO | 99/58131 A1 | 11/1999 |
| WO | 2004/041134 A1 | 5/2004 |
| WO | 2006058189 A2 | 6/2006 |
| WO | 2006093851 A2 | 9/2006 |
| WO | 2008024100 A2 | 2/2008 |
| WO | 2008106228 A2 | 9/2008 |
| WO | 2009064834 A2 | 5/2009 |
| WO | 2010005527 A1 | 1/2010 |
| WO | 2010056848 A1 | 5/2010 |
| WO | 2011085385 A1 | 7/2011 |
| WO | 2012036931 A1 | 3/2012 |
| WO | 2012051313 A2 | 4/2012 |
| WO | 2012137545 A1 | 10/2012 |
| WO | 2013003594 A3 | 1/2013 |
| WO | 2013003731 A3 | 1/2013 |
| WO | 2013006574 A1 | 1/2013 |
| WO | 2013036894 A2 | 3/2013 |
| WO | 2013114127 A1 | 8/2013 |
| WO | 2013126599 A1 | 8/2013 |
| WO | 2013149318 A1 | 10/2013 |
| WO | 2013166353 A1 | 11/2013 |
| WO | 2014049841 A1 | 4/2014 |
| WO | 2014158356 A1 | 10/2014 |
| WO | 2014179356 A1 | 11/2014 |

OTHER PUBLICATIONS

Goto, Eiki, et al., "Tear Evaporation Dynamics in Normal Subjects and Subjects with Obstructive Meibomian Gland Dysfunction," Investigative Ophthalmology & Visual Science, vol. 44, No. 2, Feb. 2003, 7 pages (pp. 533-539).

Kuscu, Naci Kemal, et al., "Tear Function Changes of Postmenopausal Women in Response to Hormone Replacement Therapy," Maturitas 44, 63-68, 2003, 6 pages.

Mori, Asako, et al., "Disposable Eyelid-Warming Device for the Treatment of Meibomian Gland Dysfunction," Jpn J Ophthalmol, vol. 47: 578-586, 2003, 9 pages (pp. 578-586).

(56) References Cited

OTHER PUBLICATIONS

Romero, Juan M., et al., "Conservative Treatment of Meibomian Gland Dysfunction," Eye and Contact Lens, vol. 30, No. 1, 2004, 6 pages (pp. 14-19).
Lemp, Michael A., et al., "The Therapeutic Role of Lipids—Managing Ocular Surface Disease," Refractive Eyecare for Ophthalmologists, vol. 9, No. 6, Jun. 2005, 14 pages.
Mori, A., et al., "Efficacy of the Treatment by the Disposable Eyelid Warming Instrument for Meibomian Gland Dysfunction," Poster Presentation, Hall A, 1 page.
Unknown, "Anatomy of the Eye and Orbit," p. 170.
Paugh, J.R. et al., "Meibomian Therapy in Problematic Contact Lens Wear," Entrez PubMed, Optom Vis Sci. Nov. 1990; 68(11): 803-6, 1 page.
Tobler, David et al., "Nanotech Silver Fights Microbes in Medical Devices," ND & DI, devicelink.com, 1 page.
Unknown, "IFU Manual for PNT Model 1000—Rev H," 24 pages.
Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.
Korb, Donald R. et al., "Tear Film Lipid Layer Thickness as a Function of Blinking," Cornea, vol. 13, No. 4, 1994, pp. 354-359.
Knop, E et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).
Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).
Friedland, B., et al., "A novel thermodynamic treatment for meibomian gland dysfunction," Current Eye Research, vol. 36, No. 2, Feb. 2011, pp. 79-87.
Non-Final Rejection mailed Jun. 17, 2009, for U.S. Appl. No. 11/434,446.
Final Rejection mailed Dec. 23, 2009, for U.S. Appl. No. 11/434,446.
Advisory Action mailed Mar. 4, 2010, for U.S. Appl. No. 11/434,446.
Non-Final Rejection mailed Apr. 9, 2010, for U.S. Appl. No. 11/434,446.
Restriction/Election Requirement mailed Oct. 1, 2010, for U.S. Appl. No. 11/434,033.
Non-Final Rejection mailed Jan. 24, 2011, for U.S. Appl. No. 11/434,033.
Korb, D. et al., "Meibomian gland therapeutic expression: quantifying the applied pressure and the limitation of resulting pain," Eye Contact Lens, vol. 37 No. 5, Sep. 2011, pp. 298-301.
Akyol-Salman, I. et al., "Comparison of the efficacy of topical N-acetyl-cysteine and a topical steroid-antibiotic combination therapy in the treatment of meibomian gland dysfunction," Journal of Ocular Pharmacology and Therapeutic, vol. 28 No. 1, Feb. 2, 2012, pp. 49-52.
No Author, "TearScience's LipiFlow Multi-center Clinical Study Shows Improved Meibomian Gland Secretions and Dry Eye Symptoms," Business Wire, Mar. 5, 2012, 2 pages.
Blackie, Caroline A. et al., "Recovery Time of an Optimally Secreting Meibomian Gland," Cornea, vol. 28, No. 3, Apr. 2009, pp. 293-297.
Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.
Paugh, Jerry R. et al., "Precorneal Residence Time of Artificial Tears Measured in Dry Eye Subjects," Optometry and Vision Science, vol. 85, No. 8, Aug. 2008, pp. 725-731.
Lemp, Michael A. et al., "Blepharitis in the United States 2009: A Survey-Based Perspective on Prevalence and Treatment." Ocul. Surf, vol. 7, No. 2 Suppl, Apr. 2009, pp. S1-S14.
Matsumoto, Yukihiro et al., "The Evaluation of the Treatment Response in Obstructive Meibomian Gland Disease by in Vivo Laser Confocal Microscopy," Graefes Arch Clin Exp Ophthalmol, vol. 247, No. 6, Jun. 2009, pp. 821-829.
Toyos, Rolando, "Intense Pulsed Light for Dry Eye Syndrome," Cataract & Refractive Surgery Today, Apr. 2009, pp. 1-3.
Donnenfeld, Eric et al., "Topical Ophthalmic Cyclosporine: Pharmacology and Clinical Uses," Survey of Ophthalmology, vol. 54, No. 3, May/Jun. 2009, pp. 321-338.
Suzuki, Tomo et al., "Estrogen and Progesterone Control of Gene Expression in the Mouse Meibomian Gland," Invest. Ophthalmol. Vis. Sci., vol. 49, No. 5, Apr. 2008, pp. 1797-1818.
Vasta, Stephanie, "Aggressive Treatments Developed for Meibomian Gland Dysfunction," Primary Care Optometry News, Nov. 1, 2009, 3 pages.
Greiner, J., "A Single LipiFlow R Thermal Pulsation System Treatment Improves Meibomian Gland Function and Reduces Dry Eye Symptoms for 9 months," Current Eye Research, vol. 37 No. 4, Apr. 2012, pp. 272-278.
Lane, S. et al., "A New System, the LipiFlow, for the Treatment of Meibomian Gland Dysfunction," Cornea, vol. 31, No. 4, Apr. 2012, pp. 396-404.
Finis, D. et al., "Meibom-Drusen-Dysfunktion," Klinische Monatsblatter fur Augenheilkunde, vol. 229, No. 5, Mar. 2012, pp. 506-513 (Abstract translated only).
Unknown, "TearScience Launches Breakthrough Technology in Canada to Address the Root Cause of Evaporative Dry Eye," Business Wire, Jun. 9, 2011, http://www.businesswire.com/news/home/20110609005860/en/TearScience-Launches-Breakthrough-Technology-Canada-Address-Root, 2 pages.
Non-final Office Action for U.S. Appl. No. 13/183,901 mailed Jun. 4, 2012, 46 pages.
Official Action Issued May, 10 2011 for Japanese Patent Application No. 2009-525529.
Partial Translation of Japanese Patent Publication No. 11-221247A, previously submitted in IDS dated Jan. 4, 2008.
Partial Translation of Japanese Patent Publication No. 2006-198249A, previously submitted in IDS dated Jan. 4, 2008.
Second Office Action for Japanese patent application 2009-525529 mailed Jun. 5, 2012, 8 pages.
Korb, et al., "Forceful meibomian gland expression with a standardized force of 8 PSI in patients with obstructive meibomian gland dysfunction," Tearscience, Date Unknown, 1 page.
Korb, et al., "Prevalence of lid wiper epitheliopathy in subjects with dry eye signs and symptoms," Cornea, vol. 29, No. 4, Apr. 2012, pp. 377-383.
Korb, et al., "Restoration of meibomian gland function post Lipiflow treatment," Tearscience, Date Unknown, 1 page.
Willis, et al., "Meibomian gland function, lid wiper epitheliopathy, and dry eye symptoms," Tearscience, Date Unknown, 1 page.
Foulks, G. et al., Comparative Effectiveness of Azithromycin and Doxycycline in Therapy of Meibomian Gland Dysfunction, ARVO Annual Meeting, May 2011, pp. 3816 (Abstract only).
Korb, et al., "Restoration of meibomian gland function post Lipiflow treatment," ARVO Annual Meeting, May 2011, pp. 3818 (Abstract only).
Maskin, S. et al., "Intraductal Meibomian Gland Probing with Adjunctive Intraductal Microtube Steriod Injection (MGPs) for Meibomian Gland Dysfuction," ARVO Annual Meeting, May 2011, pp. 3817 (Abstract only).
McCann, L. et al., "Effect of First Line Management Therapies on Dry Eye Disease," ARVO Annual Meeting, May 2011, pp. 3829 (Abstract only).
Willis, et al., Meibomian gland function, lid wiper epitheliopathy, and dry eye symptoms, ARVO Annual Meeting, May 2011, pp. 3740 (Abstact only).
Non-final Office Action for U.S. Appl. No. 13/368,976 mailed Aug. 31, 2012, 10 pages.
Non-final Office Action for U.S. Appl. No. 11/541,308 mailed Aug. 31, 2012, 20 pages.
Non-final Office Action for U.S. Appl. No. 13/242,068 mailed Aug. 29, 2012, 9 pages.

(56) References Cited

OTHER PUBLICATIONS

Non-final Office Action for U.S. Appl. No. 13/367,865 mailed Sep. 13, 2012, 9 pages.
Non-final Office Action for U.S. Appl. No. 13/367,908 mailed Sep. 13, 2012, 11 pages.
Asbell, P. et al. "The international workshop on meibomian gland dysfunction: report of the clinical trials subcommittee," Investigative Ophthalmology and Visual Science, Mar. 2011, pp. 2065-2085.
Extended European Search Report for patent application 07716441.6 mailed Sep. 4, 2012, 7 pages.
Geerling, G., et al., "The international workshop on meibomian gland dysfunction: report of the subcommittee on management and treatment of meibomian gland dysfunction," Mar. 2011, pp. 2050-2064, Investigative Ophthalmology & Visual Science, vol. 52, No. 4.
Korb, Donald R. and Blackie, Caroline A., "Meibomian gland therapeutic expression: Quantifying the applied pressure and the limitation of resulting pain," Eye and Contact Lens, Sep. 2011, pp. 298-301, vol. 37, No. 5, Philadelphia, PA.
Holifield, Karintha and Lazzaro, Douglas R., "Case report: Spontaneous stenotrophomonas maltophilia keratitis in a diabetic patient," Eye and Contact Lens, Sep. 2011, pp. 326-327, vol. 37, No. 5, Philadelphia PA.
Cunniffe, M. Geraldine et al., "Topical antiglaucoma treatment with prostaglandin analogues may precipitate meibomian gland disease," Ophthalmic Plastic and Reconstructive Surgery, Sep.-Oct. 2011, p. 128-129, vol. 27, No. 9, Lippincott Williams and Wilkins, Philadelphia, PA.
Blackie, Caroline A. et al., "Inner Eyelid Surface Temperature as a Function of Warm Compress Methodology," Optometry and Vision Science, vol. 85, No. 8, Aug. 2008, pp. 675-683.
Kokke, K.H. et al., "Oral Omega-6 Essential Fatty Acid Treatment in Contact Lens Associated Dry Eye," Contact Lens and Anterior Eye, vol. 31, No. 3, 2008, pp. 141-146.
Korb, Donald R., Slide entitled "Inner Eyelid Surface Temperature as a Function of Warm Compress Methodology," from presentation entitled "The Tear Film and Dry Eye States a Fertile Research Area," University of California at Berkeley, School of Optometry, Apr. 11, 2008. 2 pages.
Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.
Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.
Butovich, Igor et al., "Meibomian Lipid Glands and the Impact of Temperature," Investigative Opthalmology & Visual Science, vol. 51, No. 11, Nov. 2010, pp. 5508-5518.
Korb, Donald R. et al., "Restoration of Meibomian Gland Functionality with Novel Thermodynamic Treatment Device—A Case Report," Cornea, vol. 29, No. 8, Aug. 2010, pp. 930-933.
Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.
Wang, Y. et al., "Baseline Profiles of Ocular Surface and Tear Dynamics After Allogeneic Hematopoietic Stem Cell Transplantation in Patients With or Without Chronic GVHD-Related Dry Eye," Bone Marrow Transplantation, vol. 45, No. 6, Jun. 2010, pp. 1077-1083.
Korb, Donald R. et al., "Lid Wiper Epitheliopathy and Dry Eye Symptoms," Eye & Contact Lens, vol. 31, No. 1, 2005, pp. 2-8.
Foulks, Gary N., "Meibomian Gland Dysfunction: The Past, Present, and Future," Eye and Contact Lens, vol. 36, No. 5, Sep. 2010, pp. 249-253.
Blackie, Caroline A. et al., "Nonobvious Obstructive Meibomian Gland Dysfunction" Cornea, vol. 29, No. 12, Dec. 2010, pp. 1333-1345.

Haque, Reza M. et al., "Multicenter Open-label Study Evaluating the Efficacy of Azithromycin Opthalmic Solution 1% on the Signs and Symptoms of Subjects with Blepharitis," Cornea, vol. 29, No. 8, Aug. 2010, pp. 871-877.
Maskin, Steven L., "Intraductal Meibomian Gland Probing Relieves Symptoms of Obstructive Meibomian Gland Dysfunction," Cornea, vol. 29, No. 10, Oct. 2010, pp. 1145-1152.
Dausch, Eva et al., "Dry Eye Syndrome in Women's Health and Gynecology: Etiology, Pathogenesis and Current Therapeutic Strategies," Geburtshilfe and Frauenheilkunde, vol. 70, No. 9, Jan. 1, 2010, pp. 707-711. (Abstract Only).
Korb, Donald R., O.D., et al., "Meibomian Gland Dysfunction and Contact Lens Intolerance" Jnl American Optometric Association, vol. 51, No. 3, Mar. 1980, 9 pages (pp. 243-251).
Korb, Donald R. et al., "Increase in Tear Film Lipid Layer Thickness Following Treatment of Meibomian Gland Dysfunction" Lacrimal Gland, Tear Film and Dry Eye Syndromes: Basic Science Clinical Relevance. Adv. Exp. Med. Biol., vol. 350, 1994, 6 pages (pp. 293-298).
Goto, E., et al. "Treatment of Non-Inflamed Obstructive Meibomian Gland Dysfunction by an Infrared Warm Compression Device" British Journal of Ophthalmology, BJO Online, http://www.bmjjournals.com/cgi/reprintform, vol. 26, 2002, 6 pages (pp. 1402-1407).
Olson, Mary Catherine, B.A., et al., "Increase in Tear Film Lipid Layer Thickness Following Treatment with Warm Compresses in Patients with Meibomian Gland Dysfunction" Eye & Contact Lens, vol. 29(2), 2003, 6 pages.
Mitra, M. et al., "Tear Film Lipid Layer Thickness and Ocular Comfort after Meibomian Therapy via Latent Heat with a Novel Device in Normal Subjects" Eye, vol. 19, 2005, 4 pages (pp. 657-660).
Minco "Introducing: Thermofoil Heaters" Bulletin HS-202, 9 pages.
"New Over-the-Counter Dry Eye Drop Now Available to Help Estimated 40 Percent of Americans Who Suffer from Occasional or Chronic Dry Eye" Business Wire News Release, Published Mar. 31, 2008.
Gupta, S. et al. "Docetaxel-induced Meibomian Duct Inflammation and Blockage Leading to Chalazion Formation" Prostate Cancer Prostatic Diseases, vol. 10, No. 4, 2007.
Aronowicz, J D et al. "Short Term Oral Minocycline Treatment of Meibomiantis" Br. J Opthalmol, vol. 90, No. 7, Jul. 2006.
Goto, E. et al, "Treatment of Non-Inflamed Obstructive Meibomian Gland Dysfunction by an Infrared Warm Compression Device" Br J Opthalmol, vol. 86, No. 12, Dec. 2002.
"arGentis Licenses Third Treatment for Dry Eye Syndrome" www.businesswire.com, May 12, 2008.
Office Action for Japanese patent application 2009-546506 mailed Sep. 4, 2012, 6 pages.
European Search Report for patent application 06801969.4 mailed Nov. 5, 2012, 4 pages.
Examination Report for Indian patent application 563/MUMNP/2009 mailed Oct. 31, 2012, 1 pages.
Author Unknown, "New Breakthrough Treatment for Evaporative Dry Eye Disease Introduced by Dry Eye Specialist, Mark R. Mandel, M.D.," PR Newswire, Dec. 11, 2012, 2 pages, Hayward, California.
Cuevas, Miguel et al., "Correlations Among Symptoms, Signs, and Clinical Tests in Evaporative-Type Dry Eye Disease Caused by Meibomian Gland Dysfunction (MGD)," Current Eye Research, vol. 37, No. 10, Oct. 2012, pp. 855-863.
Suzuki, Tomo, "Meibomitis-Related Keratoconjunctivitis: Implications and Clinical Significance of Meibomian Gland Inflammation," Cornea, vol. 31, Supplemental Issue, Nov. 2012, pp. S41-S44.
Final Rejection for U.S. Appl. No. 13/242,068, mailed Feb. 14, 2013, 10 pages.
Examination Report for Indian Patent Application No. 564/MUMNP/2009, issued Jan. 30, 2013, 1 page.
Foulks et al., "Improving awareness, identification, and management of meibomian gland dysfunction," Ophthalmology, vol. 119, No. 10 Sup., Oct. 2012, 12 pages.
Arita, F. et al., "Comparison of the long-term effects of various topical antiglaucoma medications on meibomian glands," Cornea, vol. 31, No. 11, Nov. 2012, pp. 1229-1234.
Non-final Office Action for U.S. Appl. No. 11/931,398 mailed Nov. 2, 2012, 8 pages.

(56) References Cited

OTHER PUBLICATIONS

Examination Report issued Oct. 17, 2012, for European Application No. 07716444.0, 5 pages.
Examination Report issued Nov. 16, 2012, for European Application No. 06801969.4, 6 pages.
International Search Report mailed Jan. 7, 2013, for PCT/US12/44650, 44 pages.
Pucker, A. et al., "Analysis of Meibum and Tear Lipids," The Ocular Surface, vol. 10, No. 4, Oct. 2012, pp. 230-250.
Author Unknown, Definition of Platform, Macmillan Dictionary, accessed Dec. 10, 2012, 2 pages, http://www.macmillandictionary.com/dictionary/british/platform.
Author Unknown, Definition of Platform, Merriam-Webster Dictionary, accessed Dec. 10, 2012, 3 pages, http://www.merriam-webster.com/dictionary/platform.
Author Unknown, Definition of on, Merriam-Webster Dictionary, accessed Dec. 14, 2012, 5 pages, http://www.merriam-webster.com/dictionary/on.
Final Rejection mailed Dec. 27, 2012, for U.S. Appl. No. 13/183,901, 10 pages.
Non-Final Rejection mailed Dec. 27, 2012, for U.S. Appl. No. 12/015,593, 27 pages.
Non-Final Rejection mailed Jan. 4, 2013, for U.S. Appl. No. 12/015,600, 8 pages.
Final Office Action for U.S. Appl. No. 12/015,593 mailed Oct. 3, 2013, 21 pages.
Non-final Office Action for U.S. Appl. No. 13/183,901 mailed Oct. 4, 2013, 10 pages.
Notice of Allowance for U.S. Appl. No. 13/242,068 mailed Nov. 12, 2013, 10 pages.
Advisory Action for U.S. Appl. No. 12/015,593 mailed Dec. 13, 2013, 3 pages.
International Preliminary Report on Patentability for PCT/US2012/044650 mailed Jan. 16, 2014, 41 pages.
First Office Action for Chinese patent application 201210077169.8 mailed Nov. 26, 2013, 18 pages.
First Office Action for Chinese patent application 201210077192.7 mailed Nov. 22, 2013, 12 pages.
European Search Report for European Patent Application No. 08727830.5 issued Dec. 20, 2012, 3 pages.
Examination Report for European Patent Application No. 08727830.5 issued Jan. 15, 2013, 5 pages.
Non-final Office Action for U.S. Appl. No. 12/015,593 mailed Mar. 14, 2014, 19 pages.
First Office Action for Chinese patent application 201210127347.3 mailed Jan. 15, 2014, 13 pages.
Liu, Ze-Yuan et al., "Treatment of dry eye caused by meibomian gland dysfunction," International Eye Science, vol. 14, No. 2, Feb. 2014, pp. 270-272.
Non-final Office Action for U.S. Appl. No. 11/434,033 mailed Feb. 19, 2014, 10 pages.
Examiner's Decision of Rejection for Japanese Patent Application No. 2009-544825 mailed Jan. 7, 2014, 6 pages.
Examiner's Decision of Rejection for Japanese Patent Application No. 2009-525537 mailed Jan. 7, 2014, 6 pages.
Final Office Action for U.S. Appl. No. 13/183,901 mailed Feb. 3, 2014, 10 pages.
Lu, Hui et al., "Tear film measurement by optical reflectometry technique," Journal of Biomedical Optics, vol. 19, No. 2, Feb. 2014, 8 pages.
English translation of Final Japanese Office Action for patent application 2009-525537 mailed Jan. 29, 2013, 4 pages.
English translation of Final Japanese Office Action for patent application 2009-544825 mailed Jan. 29, 2013, 4 pages.
Aragona, P. et al., "Towards a dynamic customised therapy for ocular surface dysfunctions," British Journal of Ophthalmology, vol. 97, No. 8, Aug. 13, pp. 955-960.
Arita, R. et al., "Topical diquafosol for patients with obstructive meibomian gland dysfunction," British Journal of Ophthalmology, vol. 97, No. 6, Jun. 2013, pp. 725-729.
Greiner, J., "Long-term 12-month improvement in meibomian gland function and reduced dry eye symptoms with a single thermal pulsation treatment," Clinical and Experimental Ophthalmology, vol. 41, No. 6, Aug. 2013, pp. 524-530.
Her, Y. et al., "Dry eye and tear film functions in patients with psoriasis," Japanese Journal of Ophthalmology, vol. 57, No. 4, Jul. 2013, pp. 341-346.
Li, Li-Hu et al., "Analysis of the efficacy in the treatment of meibomian gland dysfunction," International Eye Science, vol. 13, No. 7, Jul. 2013, pp. 1495-1497.
Tang, Qin et al., "Clinical analysis of meibomian gland dysfunction in elderly patients," International Eye Science, vol. 13, No. 7, Jul. 2013, pp. 1419-1423.
Zhang et al., "Efficacy of physical therapy meibomian gland dysfunction," International Eye Science, International Journal of Ophthalmology, vol. 13, No. 6, Jun. 2013, pp. 1267-1268.
Non-final Office Action for U.S. Appl. No. 12/015,600 mailed Aug. 5, 2013, 8 pages.
Notice of Allowance for U.S. Appl. No. 12/887,165 mailed Sep. 3, 2013, 10 pages.
Notice of Allowance for U.S. Appl. No. 12/015,721 mailed Nov. 30, 2011, 8 pages.
Advisory Action for U.S. Appl. No. 12/015,721 mailed Aug. 31, 2011, 3 pages.
Final Office Action for U.S. Appl. No. 12/015,721 mailed Jun. 8, 2011, 12 pages.
Non-final Office Action for U.S. Appl. No. 12/015,721 mailed Jan. 5, 2011, 12 pages.
Notice of Allowance for U.S. Appl. No. 29/344,914 mailed Mar. 7, 2011, 7 pages.
Notice of Allowance for U.S. Appl. No. 29/344,914 mailed Jan. 12, 2011, 7 pages.
English translation of Japanese Office Action for patent application 2009-525536 mailed Jan. 10, 2012, 6 pages.
International Search Report for PCT/US07/00493 mailed Oct. 1, 2007, 1 page.
English translation of First Office Action for Chinese patent application 200780039253.8 mailed Jul. 12, 2010, 6 pages.
Extended European Search Report for PCT/US2007/000525 mailed Sep. 20, 2010, 11 pages.
English translation of Japanese Office Action for patent application 2009-544825 mailed Jan. 10, 2012, 9 pages.
International Search Report for PCT/US07/00525 mailed Dec. 3, 2007, 12 pages.
Extended European Search Report for patent application 07716445.7 mailed Apr. 7, 2011, 9 pages.
English translation of Japanese Office Action for patent application 2009-525537 mailed Jan. 10, 2012, 4 pages.
International Search Report for PCT/US07/0050508 mailed Nov. 2, 2007, 1 page.
English translation of Second Chinese Office Action for patent application 200880008741.7 mailed Mar. 29, 2012, 7 pages.
English translation of First Chinese Office Action for patent application 200880008741.7 mailed Jul. 20, 2011, 7 pages.
Office Action for Israeli patent application 199920 mailed May 22, 2011, 2 pages.
International Search Report for PCT/US08/51309 mailed May 20, 2008, 1 page.
English translation of First Office Action for Chinese patent application 200680056181.3 mailed Jun. 12, 2010, 6 pages.
Final Office Action for U.S. Appl. No. 13/368,976 mailed Mar. 11, 2013, 8 pages.
International Search Report for PCT/US06/32544 mailed May 12, 2008, 8 pages.
Korb, et al., "Forceful Meibomian Gland Expression with a Standardized Force of 8 PSI in Patients with Obstructive Meibomian Gland Dysfunction," ARVO Annual Meeting, Poster Session, Program No. 3819, Poster Board No. D952, May 3, 2011, 2 pages. (Abstract Only).
Advisory Action for U.S. Appl. No. 11/931,398 mailed May 15, 2013, 2 pages.
Non-final Office Action for U.S. Appl. No. 12/887,165 mailed Apr. 10, 2013, 13 pages.

(56) References Cited

OTHER PUBLICATIONS

Notice of Allowance for U.S. Appl. No. 13/367,865 mailed May 23, 2013, 9 pages.
Advisory Action for U.S. Appl. No. 13/367,908 mailed May 22, 2013, 3 pages.
Examination Report for Indian Patent Application No. 555/MUMNP/2009, issued Apr. 15, 2013, 1 page.
Advisory Action for U.S. Appl. No. 11/541,308 mailed Jun. 26, 2013, 3 pages.
Translation of Notice of Rejection for Japanese Patent Application No. 2009-525529 mailed May 14, 2013, 5 pages.
Non-final Office Action for U.S. Appl. No. 11/434,033 mailed Aug. 12, 2011, 8 pages.
Final Office Action for U.S. Appl. No. 11/434,033 mailed Mar. 15, 2012, 9 pages.
Non-final Office Action for U.S. Appl. No. 11/931,398 mailed Jan. 27, 2012, 4 pages.
Notice of Allowance for U.S. Appl. No. 13/025,951 mailed Mar. 28, 2012, 8 pages.
Non-final Office Action for U.S. Appl. No. 13/025,951 mailed Oct. 25, 2011, 9 pages.
Notice of Allowance for U.S. Appl. No. 13/025,990 mailed Mar. 28, 2010, 9 pages.
Non-final Office Action for U.S. Appl. No. 13/025,990 mailed Oct. 25, 2011, 11 pages.
Notice of Allowance for U.S. Appl. No. 11/434,054 mailed Oct. 18, 2011, 9 pages.
Non-final Office Action for U.S. Appl. No. 11/434,054 mailed May 26, 2011, 7 pages.
Non-final Office Action for U.S. Appl. No. 11/434,054 mailed Sep. 8, 2011, 7 pages.
Non-final Office Action for U.S. Appl. No. 11/434,054 mailed Mar. 12, 2010, 7 pages.
Notice of Allowance for U.S. Appl. No. 12/821,183 mailed Jul. 29, 2011, 8 pages.
Non-final Office Action for U.S. Appl. No. 12/821,183 mailed May 26, 2011, 8 pages.
Non-final Office Action for U.S. Appl. No. 12/821,183 mailed Dec. 21, 2010, 7 pages.
Notice of Allowance for U.S. Appl. No. 11/541,291 mailed May 26, 2011, 7 pages.
Notice of Allowance for U.S. Appl. No. 11/541,291 mailed Jan. 10, 2011, 6 pages.
Final Office Action for U.S. Appl. No. 11/541,291 mailed Aug. 17, 2010, 6 pages.
Non-final Office Action for U.S. Appl. No. 11/541,291 mailed Jun. 2, 2010, 10 pages.
Advisory Action for U.S. Appl. No. 11/541,291 mailed Mar. 30, 2010, 3 pages.
Final Office Action for U.S. Appl. No. 11/541,291 mailed Dec. 16, 2010, 11 pages.
Non-final Office Action for U.S. Appl. No. 11/541,291 mailed May 19, 2009, 16 pages.
Notice of Allowance for U.S. Appl. No. 11/931,646 mailed Aug. 5, 2010, 6 pages.
Advisory Action for U.S. Appl. No. 11/931,646 mailed Mar. 30, 2012, 3 pages.
Final Office Action for U.S. Appl. No. 11/931,646 mailed Dec. 15, 2009, 11 pages.
Non-final Office Action for U.S. Appl. No. 11/931,646 mailed May 19, 2009, 11 pages.
Notice of Allowance for U.S. Appl. No. 11/541,418 mailed May 26, 2011, 7 pages.
Advisory Action for U.S. Appl. No. 11/541,418 mailed Apr. 6, 2011, 3 pages.
Final Office Action for U.S. Appl. No. 11/541,418 mailed Mar. 10, 2011, 21 pages.
Non-final Office Action for U.S. Appl. No. 11/541,418 mailed Jul. 12, 2012, 20 pages.
Notice of Allowance for U.S. Appl. No. 12/015,558 mailed Jun. 1, 2011, 8 pages.
Non-final Office Action for U.S. Appl. No. 12/015,558 mailed Aug. 13, 2010, 9 pages.
Non-final Office Action for U.S. Appl. No. 11/928,681 mailed Feb. 2, 2012, 4 pages.
Notice of Allowance for U.S. Appl. No. 29/303,312 mailed Mar. 1, 2010, 7 pages.
Notice of Allowance for U.S. Appl. No. 29/303,314 mailed Feb. 5, 2010, 6 pages.
Final Office Action for U.S. Appl. No. 29/303,314 mailed Dec. 28, 2009, 6 pages.
Notice of Allowance for U.S. Appl. No. 29/303,317 mailed Feb. 1, 2010, 8 pages.
Non-final Office Action for U.S. Appl. No. 29/303,317 mailed Sep. 1, 2009, 10 pages.
Notice of Allowance for U.S. Appl. No. 12/015,567 mailed May 20, 2011, 8 pages.
Non-final Office Action for U.S. Appl. No. 12/015,567 mailed Aug. 16, 2011, 9 pages.
Notice of Allowance for U.S. Appl. No. 12/015,576 mailed May 20, 2011, 8 pages.
Non-final Office Action for U.S. Appl. No. 12/015,576 mailed Jul. 19, 2010, 11 pages.
Notice of Allowance for U.S. Appl. No. 12/015,584 mailed Jul. 8, 2011, 4 pages.
Notice of Allowance for U.S. Appl. No. 12/015,584 mailed Jun. 29, 2011, 7 pages.
Final Office Action for U.S. Appl. No. 12/015,584 mailed May 27, 2011, 7 pages.
Non-final Office Action for U.S. Appl. No. 12/015,584 mailed Aug. 23, 2010, 9 pages.
Non-final Office Action for U.S. Appl. No. 12/015,600 mailed Mar. 19, 2012, 6 pages.
Notice of Allowance for U.S. Appl. No. 12/015,675 mailed Oct. 26, 2011, 9 pages.
Non-final Office Action for U.S. Appl. No. 12/015,675 mailed May 10, 2011, 7 pages.
Notice of Allowance for U.S. Appl. No. 12/015,683 mailed Oct. 26, 2011, 8 pages.
Non-final Office Action for U.S. Appl. No. 12/015,683 mailed May 6, 2011, 14 pages.
Agnifili et al., "In vivo confocal microscopy of meibomian glands in glaucoma," British Journal of Ophthalmology, vol. 97, No. 3, Mar. 2013, pp. 343-349, United Kingdom.
Khandelwal, et al., "Androgen regulation of gene expression in human meibomian gland and conjunctival epithelial cells," Molecular Vision, vol. 18, Apr. 27, 2012, pp. 1055-1067.
Final Office Action for U.S. Appl. No. 11/541,308 mailed Mar. 19, 2013, 25 pages.
Final Office Action for U.S. Appl. No. 11/931,398 mailed Mar. 4, 2013, 7 pages.
Advisory Action for U.S. Appl. No. 13/183,901 mailed Mar. 11, 2013, 3 pages.
Final Office Action for U.S. Appl. No. 13/242,068 mailed Feb. 14, 2013, 10 pages.
Final Office Action for U.S. Appl. No. 13/367,865 mailed Mar. 4, 2013, 7 pages.
Final Office Action for U.S. Appl. No. 13/367,908 mailed Feb. 27, 2013, 7 pages.
Yoshitomi, et al., "Meibomian Gland Compressor and Cataract Surgery," New Ophthalmology, Japan, 2001, vol. 18, No. 3, pp. 321-323.
Advisory Action for U.S. Appl. No. 13/368,976 mailed Jul. 10, 2013, 3 pages.
Non-final Office Action for U.S. Appl. No. 13/242,068 mailed Jul. 3, 2013, 7 pages.
Notice of Allowance for U.S. Appl. No. 13/367,908 mailed Aug. 19, 2013, 8 pages.
Notice of Allowance for U.S. Appl. No. 13/368,976 mailed Aug. 30, 2013, 9 pages.

(56) References Cited

OTHER PUBLICATIONS

Purslow, Christine, "Evaluation of the ocular tolerance of a novel eyelid-warming device used for meibomian gland dysfunction," Contact Lens & Anterior Eye, vol. 36, No. 5, Elsevier Ltd., Oct. 2013, pp. 226-231.
Final Office Action for U.S. Appl. No. 12/015,600 mailed Apr. 29, 2014, 9 pages.
Advisory Action and Applicant-Initiated Interview Summary for U.S. Appl. No. 13/183,901 mailed Apr. 21, 2014, 5 pages.
First Office Action for Chinese patent application 201310017764.7 issued Mar. 31, 2014, 20 pages.
First Office Action for Chinese patent application 201310017761.3 issued May 6, 2014, 12 pages.
Second Office Action for Chinese patent application 201210077169.8 issued May 20, 2014, 3 pages (no translation).
Final Office Action for U.S. Appl. No. 11/434,033 mailed Jun. 2, 2014, 11 pages.
Non-final Office Action for U.S. Appl. No. 11/931,398 mailed Jun. 3, 2014, 8 pages.
Non-final Office Action for U.S. Appl. No. 11/931,914 mailed Jun. 10, 2014, 15 pages.
Second Office Action for Chinese patent application 201210077192.7 mailed May 5, 2014, 3 pages.
Notice of Allowance for U.S. Appl. No. 11/434,033 mailed Aug. 8, 2014, 8 pages.
Final Office Action for U.S. Appl. No. 12/015,593 mailed Jul. 7, 2014, 19 pages.
Advisory Action for U.S. Appl. No. 12/015,600 mailed Jul. 16, 2014, 3 pages.
Examination Report for European Patent Application No. 07716441.6 mailed May 19, 2014, 4 pages.
Advisory Action for U.S. Appl. No. 12/015,593, mailed Oct. 16, 2014, 3 pages.
Second Office Action for Chinese Patent Application No. 201310017764.7, issued Nov. 15, 2014, 12 pages.
Lin, Hui et al., "Dry eye disease: A review of diagnostic approaches and treatments," Saudi Journal of Ophthalmology, vol. 28, Issue 3, Jul.-Sep. 2014, Saudi Ophthalmological Society, pp. 173-181.
Ozer, P.A. et al., "Eyelid nodule in a child: a chalazion or idiopathic facial aseptic granuloma?" Eye, vol. 28, No. 9, Sep. 2014, The Royal College of Ophthalmologists, pp. 1146-1147.
Non-Final Office Action for U.S. Appl. No. 12/015,600 mailed Oct. 31, 2014, 9 pages.

* cited by examiner

TREATMENT OF OBSTRUCTIVE DISORDERS OF THE EYE OR EYELID

RELATED APPLICATIONS

This application is a continuation-in-part application of U.S. patent application Ser. No. 11/541,418, now issued as U.S. Pat. No. 7,981,145, filed Sep. 29, 2006, entitled "Treatment of Meibomian Glands" to Korb et al., which claims priority benefit of U.S. patent application Ser. No. 11/434,033, filed May 15, 2006, entitled "Method and Apparatus for Treating Gland Dysfunction Employing Heated Medium" to Grenon et al. and U.S. patent application Ser. No. 11/434,054, filed May 15, 2006, entitled "Method and Apparatus for Treating Meibomian Gland Dysfunction" to Korb et al., both of which claim priority benefit of U.S. Provisional Application Ser. No. 60/700,233, filed Jul. 18, 2005.

This application is also a continuation-in-part application of U.S. patent application Ser. No. 11/434,054, now issued as U.S. Pat. No. 8,083,787, filed May 15, 2006, entitled "Method and Apparatus for Treating Meibomian Gland Dysfunction" to Korb et al., which claims priority benefit of U.S. Provisional Application Ser. No. 60/700,233, filed Jul. 18, 2005.

This application is also a continuation-in-part application of U.S. patent application Ser. No. 11/434,033, filed May 15, 2006, entitled "Method and Apparatus for Treating Gland Dysfunction Employing Heated Medium" to Grenon et al., which claims priority benefit of U.S. Provisional Application Ser. No. 60/700,233, filed Jul. 18, 2005.

This application is also a continuation-in-part application of U.S. patent application Ser. No. 11/434,446, now abandoned, filed May 15, 2006, entitled "Method and Apparatus for Treating Gland Dysfunction" to Korb et al., which claims priority benefit of U.S. Provisional Application Ser. No. 60/700,233, filed Jul. 18, 2005.

This application is also a continuation-in-part application of U.S. patent application Ser. No. 11/541,291, now issued as U.S. Pat. No. 7,981,095, filed Sep. 29, 2006, entitled "Method and Apparatus for Treating Meibomian Gland Dysfunction Employing Fluid Jet" to Grenon et al., which claims priority benefit of U.S. patent application Ser. No. 11/434,033, filed May 15, 2006, entitled "Method and Apparatus for Treating Gland Dysfunction Employing Heated Medium" to Grenon et al., which claims priority benefit of U.S. Provisional Application Ser. No. 60/700,233, filed Jul. 18, 2005.

This application is also a continuation-in-part application of U.S. patent application Ser. No. 11/541,308, filed Sep. 24, 2006, entitled "Melting Meibomian Gland Obstructions" to Korb et al., which claims priority benefit of U.S. patent application Ser. No. 11/434,054, filed May 15, 2006, entitled "Method and Apparatus for Treating Meibomian Gland Dysfunction" to Korb et al., which claims priority benefit of U.S. Provisional Application Ser. No. 60/700,233, filed Jul. 18, 2005.

All of the aforementioned applications and their priority applications are hereby incorporated by reference herein in their entireties.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

FIELD OF THE INVENTION

This invention relates generally to treatment of mammalian eyes. More particularly, this invention relates to treatments of obstructive disorders of the eye such as obstruction of meibomian glands, chalazion, hordeolum, pimples, blackheads, styes and other disorders characterized by obstruction of a gland or other passage or opening of the eye or eyelid structures for example, by use of various combinations of heat to melt certain obstructions (or melt material binding solid particles forming an obstruction), mechanical or other action to clear the obstruction, and pharmaceutical treatment once the obstruction has been cleared.

BACKGROUND OF THE INVENTION

The human body contains a number of glands including the lacrimal and meibomian glands of the eye, the sebaceous or pilo-sebaceous hair glands on the face and underarms, sweat glands, tear ducts, and the mammary glands in the breasts. These glands may malfunction due to age, irritation, environmental conditions, cellular debris, inflammation, hormonal imbalance and other causes. One common disease state of the eyelid glands is the restriction or stoppage of the natural flow of fluid out of the gland caused by an obstruction.

In the human eye, the tear film covering the ocular surfaces is composed of three layers. The innermost layer in contact with the ocular surface is the mucus layer comprised of many mucins. The middle layer comprising the bulk of the tear film is the aqueous layer, and the outermost layer is a thin (less than 250 nm) layer comprised of many lipids known as "meibum" or "sebum." The sebum is secreted by the meibomian glands, enlarged specialized sebaceous-type glands (hence, the use of "sebum" to describe the secretion) located within both the upper and lower eyelids, with orifices designed to discharge the lipid secretions onto the lid margins, thus forming the lipid layer of the tear film. The typical upper eyelid has about 25 meibomian glands and the lower eyelid has about 20 meibomian glands, which are somewhat larger than those located in the upper lid. The meibomian gland comprises various sac-like acini which discharge the secretion into the main central duct of the gland. The secretion then passes into the orifices which are surrounded by smooth muscle tissue and the muscle of Riolan which are presumed to aid in the expression of sebum. The meibomian gland orifices open onto the lid margin at and around the junction of the inner mucous membrane and the outer skin of the eyelids termed the mucocutaneous junction.

Specifically, as illustrated in the above patent applications, each meibomian gland has a straight long central duct lined with four epithelial layers on the inner surface of the duct. Along the length of the central duct there are multiple lateral out-pouching structures, termed acini where the secretion of the gland is manufactured. The inner lining of each acinus differs from the main central duct in that these specialized cells provide the secretions of the meibomian gland. The secretions flow from each acinus to the duct. While it has not been established with certainty, there appears to be a valve system between each acinus and the central duct to retain the secretion until it is required, at which time it is discharged in to the central duct. The meibomian secretion is then stored in the central duct and is released through the orifice of each gland onto the lid margin. Blinking and the squeezing action of the muscle of Riolan surrounding the meibomian glands are thought to be the primary mechanism to open the orifice for the release of secretion from the meibomian gland.

The upward phase of blinking causes the upper lid to pull a sheet of the lipids secreted by the meibomian glands upward and over the other two layers of the tear film, thus forming a type of protective coating which limits the rate at which the underlying layers evaporate. Thus, it will be seen that a defective lipid layer or an incorrect quantity of such lipids can result in accelerated evaporation of the aqueous layer which, in turn, causes symptoms such as itchiness, burning, irritation, and dryness, which are collectively referred to as "dry eye."

Dry eye states have many etiologies. A common cause of common dry eye states is a disorder where the glands are obstructed or occluded, usually referred to as "meibomian gland dysfunction" (MGD). As employed herein the terms "occluded" and "obstruction" as they relate to meibomian gland dysfunction are defined as partially or completely blocked or plugged meibomian glands, or any component thereof, having a solid, semi-solid, or thickened congealed secretion and/or plug, leading to a compromise, or more specifically, a decrease or cessation of secretion. Also with a reduced or limited secretion, the meibomian gland may be compromised by the occluded or obstructive condition as evidenced by a yellowish color indicating a possible infection state, or may be otherwise compromised so that the resulting protective lipid protective film is not adequate.

Meibomitis, an inflammation of the meibomian glands which sometimes leads to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstructions which partially or completely block the meibomian gland orifices and/or the central duct (canal) of the gland, or possibly the acini or acini valves (assuming they do in fact exist) or the acini's junction with the central duct. Such obstructions compromise the secretory functions of the individual meibomian glands. More particularly, these keratotic obstructions can comprise combinations of bacteria, sebaceous ground substance, dead, and/or desquamated epithelial cells (see Korb et al., Meibomian Gland Dysfunction and Contact Lens Intolerance, Journal of the Optometric Association, Vol. 51, Number 3, (1980), pp. 243-251). While meibomitis is obvious by inspection of the external lids, meibomian gland dysfunction may not be obvious even when examined with the magnification of the slit-lamp biomicroscope, since there may not be external signs, or the external signs may be so minimal that they are overlooked. The external signs of meibomian gland dysfunction without obvious lid inflammation may be limited to subtle alterations of the meibomian gland orifices, overgrowth of epithelium over the orifices, and pouting of the orifices of the glands with congealed material acting as obstructions. In severe instances of meibomian gland dysfunction without obvious lid inflammation the changes may be obvious, including serrated or undulated lid margins, orifice recession and more obvious overgrowth of epithelium over the orifices, and pouting of the orifices.

Hormonal changes, which occur during menopause, and particularly changing estrogen levels, can result in thickening of the oils secreted by the meibomian glands which results in clogged gland orifices. Further, decreased estrogen levels may also enhance conditions under which *staphylococcal* bacteria can proliferate. This can cause migration of the bacteria into the glands, thus resulting in a decreased secretion rate.

When the flow of secretions from the meibomian gland is restricted due to the existence of an obstruction, cells on the eyelid margin have been observed to grow over the gland orifice, thus further restricting sebum flow and exacerbating the dry eye condition. Additional factors which may cause or exacerbate meibomian gland dysfunction include age, disorders of blinking, activities such as computer use which compromise normal blinking, contact lens wear and hygiene, cosmetic use, or other illness, particularly diabetes.

The state of an individual meibomian gland can vary from optimal, where clear meibomian fluid is produced, to mild or moderate meibomian gland dysfunction where milky fluid or inspissated or creamy secretion is produced, to total blockage where no secretion of any sort can be obtained (see Korb et al., "Increase in Tear Film Lipid Layer Thickness Following Treatment of Meibomian Gland Dysfunction," Lacrimal Gland, tear Film, and Dry Eye Syndromes, pp. 293-298, Edited by D. A. Sullivan, Plenum Press, New York (1994)). Significant chemical changes of the meibomian gland secretions occur with meibomian gland dysfunction and consequently, the composition of the naturally occurring tear film is altered, which in turn, contributes to ocular disease which is generally known as "dry eye."

While the tear film operates as a singular entity and all of the layers thereof are important, the lipid layer, which is secreted from the meibomian glands, is of particular significance as it functions to slow the evaporation of the underlying layers and to lubricate the eyelid during blinking which prevents dry eye.

Thus, to summarize, the meibomian glands of mammalian (e.g., human) eyelids secrete oils that prevent evaporation of the tear film and provide lubrication to the eye and eyelids. These glands can become blocked or plugged by various mechanisms leading to so-called "dry eye syndrome." While not the only cause, meibomian gland dysfunction (MGD) is known to be a major cause of dry eye syndrome. The disorder is characterized by a blockage of some sort within the meibomian glands or at their surface preventing normal lipid secretions from flowing from the meibomian glands to form the lipid layer of the tear film.

Such secretions serve to prevent evaporation of the tear film and lubricate the eye and eyelids, hence their absence can cause dry eye syndrome. Obstructions or occlusions of the meibomian glands may be present over or at the orifice of the gland, in the main channel of the gland which may be narrowed or blocked, or possibly in other locations including the passages from the acini to the main channel.

It has been theorized that the acini of the glands may have valves at their junction with the main channel of the gland. The inventors theorize that if these valves exist, they may also become obstructed in some instances leading to reduced or blocked flow from the acini. These obstructions or occlusions may have various compositions.

In response to the foregoing, various treatment modalities have been developed in order to treat the dry eye condition, including drops which are intended to replicate and replace the natural tear film, pharmaceuticals which are intended to stimulate the tear producing cells, and various heating devices which are designed to assist in unclogging the meibomian glands. Other techniques involve manual expression of the glands.

Eye drops such as Refresh®, Soothe®, and Systane® brand eye drops are designed to closely replicate the naturally occurring healthy tear film. However, their use and administration is merely a treatment of symptoms and not of the underlying cause. Further, the use of drops is generally for an indefinite length of time and consequently, extended use can become burdensome and costly.

Pharmaceutical modalities such as the use of tetracycline have also been suggested to treat meibomian gland dysfunction and one such treatment is disclosed in U.S. Patent Application Publication No. 2003/0114426 titled "Method for Treating Meibomian Gland Disease," U.S. Pat. No. 6,455,583 titled "Method for Treating Meibomian Gland Disease" to Pflugfelder et al., and PCT Publication No. WO 99/58131 titled "Use of Tetracyclines for Treating Meibomian Gland Disease." However, this treatment has not proven to be universally clinically effective, and it may be unnecessary in cases where meibomian gland dysfunction is the result of obstruction of the gland without infection. The use of corticosteroids have also been proposed to treat meibomian gland dysfunction as disclosed in U.S. Pat. No. 6,153,607 titled "Non-preserved Topical Corticosteroid for Treatment of Dry Eye, filamentary Keratitis, and Delayed Tear Clearance (or Turnover)" to Pflugfelder et al. Again, this proposed treatment appears to treat the symptom of dry eye, as opposed to treatment of the underlying cause. Additionally, the use of topically applied androgens or androgen analogues have also been used to treat acute dry eye signs and symptoms in Keratoconjuctivitis Sicca as disclosed in U.S. Pat. No. 5,958,912 and U.S. Pat. No. 6,107,289 both titled "Ocular Therapy in Keratoconjunctivitis Sicca Using Topically Applied Androgens or TGF-β" and both issued to Sullivan.

Most knowledgeable doctors agree that heat is beneficial in treating MGD. Depending upon the nature of the obstruction, heat may be beneficial in actually melting or loosening the obstructing material, permitting the gland to begin production and excretion of lipids and other fluids more freely.

One modality for the heat treatment of meibomian gland dysfunction is disclosed in European Patent Application Serial No. PCT/GB2003/004782 titled "Eyelid Margin Wipes Comprising Chemical Means for Temperature Adjustment." As disclosed in this patent application, a wipe is provided wherein prior to use, a chemical agent is activated that will heat the wipe to about 32° C. to about 40° C. The hot wipe is then applied to the lids and manual expression can then be used to unclog the ducts. This method is not without its drawbacks in that lid irritation can be exacerbated by nonspecific heating.

Another method of heating the eyelids and meibomian glands uses near infrared (NIR) radiation. More specifically, two hard eye patches were attached to an eye mask according to the pupillary distance of the subject. The eye mask was held in place by an elastic headband. Each patch employed 19 light emitting diodes, emitting near infrared radiation from 850 nm to 1050 nm, with a peak at 940 nm. The device produced 10 mW/cm$^2$ of energy operating on electrical power (Goto et al., Treatment of Non-Inflamed Obstructive Meibomian Gland dysfunction by an Infrared Warm Compression Device, British Journal of Ophthalmology, Vol. 86 (2002), pp. 1403-1407). This device is designed as a non-contact infrared heating mask using IR light emitting diodes. However, there are many potential problems with use of an IR heating mechanism. For example, the IR Heat can penetrate beyond the eyelid into the cornea which is undesirable, and could ultimately cause cataracts or other damage. Additionally, the IR mask heater places no pressure whatsoever on the eyelid (despite the description as a compression device) which we have determined is useful to expel the blockage. Moreover, tests conducted on a sample of this mask revealed that in spite of the potential dangers, the mask produced very little actual heat.

U.S. Patent Application Publication No. 2004/0237969 titled "Therapeutic Eye and Eye Lid Cover" comprises a pair of goggles that are adapted to deliver heated saturated air to the eyelids and particularly to the meibomian glands, again to heat the gland. Heat treatment of the eyes is also discussed in the article titled "Tear Film Lipid Layer Thickness and Ocular Comfort after Meibomian Therapy via Latent Heat with a Novel Device in Normal Subjects" by Mitra et al., published in Eye, (2004) at pages 1-4.

U.S. Patent Application Publication No. 2003/0233135 titled "Method and Apparatus for Preventing and Treating Eyelid Problems" to Yee attempts to clear the plugged meibomian glands by means of electrical stimulation of the muscle of Riolan which the invention presumed to aid in the expression of the meibomian gland secretion.

MGD is a substantial but not isolated condition falling into the general category of obstructive disorders of the eye and/or eyelid. Other disorders, such as for example without limitation chalazion, hordeolum, pimples, blackheads, and styes, are characterized by obstruction of a gland or other passage or opening of the eye or eyelid structure. These disorders, along with MGD, are collectively referred to herein as obstructive disorders and can cause substantial pain and discomfort as well as interference with the normal function of the eye.

SUMMARY OF THE EMBODIMENTS

It is an object of certain embodiments consistent with the present invention to provide a method for treatment of mammalian eyes or eyelids. This treatment includes, but is not limited to, treatment for Meibomian Gland Dysfunction (MGD).

It is another object of certain embodiments consistent with the present invention to provide a method of treatment that first produces a flow of fluids that are blocked by an obstructive disorder of the eye, eyelids, or related structures, including but not limited to obstructions in glands or other openings in the eye or eyelids. In certain embodiments, once the flow of fluids is produced, pharmacological treatment can be used to assist in maintaining the flow of fluids or otherwise promote healing of the disorder.

In accordance with certain illustrative embodiments consistent with the invention, a method of treating obstructive disorders of a structure of an eye or eyelid involves applying regulated heat to the structure containing the obstructive disorder that reaches a temperature adequate to melt obstructions in the structure and place the obstructions in a melted state, maintaining the heat for a time period adequate to melt the obstructions and place the obstructions in the melted state, and mechanically or otherwise treating the structure by expressing melted obstructions from the glands, wherein the treating is carried out either during the time period or after the time period but while the obstruction remains in the melted state. In certain embodiments, the method further involves subsequently treating the structure by use of a pharmacological agent. In certain embodiments, the time period comprises approximately 1 to 60 minutes. In certain embodiments, the treatment is carried out using a heated instrument. In certain embodiments, the temperature reaches approximately 45 degrees Celsius. In certain embodiments, the temperature reaches between approximately 42 and 47 degrees Celsius. In certain embodiments, the temperature is at least 37 degrees Celsius. In certain embodiments, the treating is carried out within 3 minutes after the end of the time period. In certain embodiments, the treatment is carried out by at least one of milkingly expressing the melted obstruction from the structure of eyes or eyelids, applying mechanical energy stimulation to the structure, and/or squeezing the structure and applying constant pressure to the structure. In certain embodiments, a pharmacological agent may be used to promote the free flow of the structure and/or to reduce re-obstruction. In certain embodiments, the pharmacological agent comprises a topical pharmacological agent. In certain embodiments, the pharmacological agent comprises a systemic pharmacological agent. In certain embodiments, the pharmacological agent is selected from the group consisting of anti-inflammatory agents, antibiotics, topical tetracycline, oral tetracycline, topical corticosteroids, oral corticosteroids, topical androgens, topical androgen analogues, TGF-β, omega 3 compounds, enzymes that promote lipid production, agents that stimulate production of enzymes that promote lipid production, agents that act as a secretagogue to enhance Meibomian gland secretion, and agents that replace or promote production of any tear component. In certain embodiments, a plurality of pharmacological agents are selected. In certain embodiments, the process further involves repeating the applying and maintaining of regulated heat after a time interval to maintain flow of fluids from the structure. In certain embodiments, the process further involves repeating the treating at the time interval to maintain flow of fluids from the structure. In certain embodiments, the obstructive disorder can be chalazion, hordeolum, pimples, blackheads, or styes, as examples.

In another embodiment, a method of treating obstructive disorders of a structure of the eye or eyelid involves applying a regulated heat of at least approximately 37 degrees Celsius to the structure containing the obstruction to a temperature adequate to melt obstructions in the structure and place such obstructions in a melted state, maintaining the heat for a time period adequate to melt the obstructions and place the obstructions in the melted state, and wherein the time period is between approximately 1 and 60 minutes, treating mechanically or otherwise the structure by expressing the melted obstructions from the structure, wherein the mechanical or other treating is carried out prior to 90 seconds after expiration of the time period and while the obstruction remains in the melted state, and subsequently pharmacologically treating the structure by use of a pharmacological agent. A pharmacological agent may be used to promote the free flow of the structure and/or to reduce re-obstruction. In certain embodiments, the method further involves subsequently treating the structure by use of a pharmacological agent. In certain embodiments, the time period comprises approximately 1 to 60 minutes. In certain embodiments, the treatment is carried out using a heated instrument. In certain embodiments, the temperature reaches approximately 45 degrees Celsius. In certain embodiments, the temperature reaches between approximately 42 and 47 degrees Celsius. In certain embodiments, the temperature is at least 37 degrees Celsius. In certain embodiments, the treating is carried out within 3 minutes after the end of the time period. In certain embodiments, the treatment is carried out by at least one of milkingly expressing the melted obstruction from the structure, applying mechanical or other energy stimulation to the structure, and/or squeezing the structure and applying constant pressure to the structure. In certain embodiments, the pharmacological agent comprises a topical pharmacological agent. In certain embodiments, the pharmacological agent comprises a systemic pharmacological agent. In certain embodiments, the pharmacological agent is selected from the group consisting of anti-inflammatory agents, antibiotics, topical tetracycline, oral tetracycline, topical corticosteroids, oral corticosteroids, topical androgens, topical androgen analogues, TGF-β, omega 3 compounds, enzymes that promote lipid production, agents that stimulate production of enzymes that promote lipid production, agents that act as a secretagogue to enhance Meibomian gland secretion, and agents that replace or promote production of any tear component. In certain embodiments, a plurality of pharmacological agents are selected. In certain embodiments, the process further involves repeating the applying and maintaining of regulated heat after a time interval to maintain flow of fluids from the structure. In certain embodiments, the process further involves repeating the treating at the time interval to maintain flow of fluids from the structure. In certain embodiments, the obstructive disorder can be chalazion, hordeolum, pimples, blackheads, or styes.

Another method of treating obstructive disorders of a structure of the eye or eyelid involves applying a regulated heat in the range of approximately 42 to 47 degrees Celsius to the structure containing the obstruction to a temperature adequate to melt obstructions in the structure and place the obstructions in a melted state, maintaining the heat for a time period adequate to melt the obstructions and place the obstructions in the melted state, wherein the time period is between approximately 1 and 60 minutes, mechanically or otherwise treating the structure by expressing fluid or suspension from the glands, wherein the treating is carried out either during the time period or within 90 seconds following the end of the time period while the obstruction remains in the melted state, wherein the treating is carried out using a heated instrument, and subsequently, pharmacologically treating the structure by use of a pharmacological agent.

A method of treating obstructive disorders of a structure of the eye or eyelid including chalazion, hordeolum, pimples, blackheads, and styes in which an obstruction blocks flow of fluid from the structure which involves applying a regulated heat source proximate to the structure for a selected time and at a selected temperature adequate to soften or liquefy at least a portion of the obstruction, mechanically or otherwise treating the structure while the at least a portion of the obstruction remains softened or liquefied such that at least a portion of the obstruction is removed, and subsequently treating the disorder with a pharmacological agent.

In certain embodiments of the above methods, the method can incorporate subsequently treating the structure by use of a pharmacological agent. In certain embodiments, the time period comprises approximately 1 to 60 minutes. In certain embodiments, the treatment is carried out using a heated instrument. In certain embodiments, the temperature reaches approximately 45 degrees Celsius. In certain embodiments, the temperature reaches between approximately 42 and 47 degrees Celsius. In certain embodiments, the temperature is at least 37 degrees Celsius. In certain embodiments, the treating is carried out within 3 minutes after the end of the time period. In certain embodiments, the treatment is carried out by at least one of milkingly expressing the melted obstruction from the structure, applying mechanical or other energy form stimulation to the structure, and/or squeezing the structure and applying constant pressure to the structure. In certain embodiments, a pharmacological agent may be used to promote the free flow of the structure and/or to reduce re-obstruction. In certain embodiments, the pharmacological agent comprises a topical pharmacological agent. In certain embodiments, the pharmacological agent comprises a systemic pharmacological agent. In certain embodiments, the pharmacological agent is selected from the group consisting of anti-inflammatory agents, antibiotics, topical tetracycline, oral tetracycline, topical corticosteroids, oral corticosteroids, topical androgens, topical androgen analogues, TGF-β, omega 3 compounds, enzymes that promote lipid production, agents that stimulate production of enzymes that promote lipid production, agents that act as a secretagogue to enhance Meibomian gland secretion, and agents that replace or promote production of any tear component. In certain embodiments, a plurality of pharmacological agents are selected. In certain embodiments, the process further involves repeating the applying and maintaining of regulated heat after a time interval to maintain flow of fluids from the structure. In certain embodiments, the process further involves repeating the treating at the time interval to maintain flow of fluids from the structure. In certain embodiments, the obstructive disorder can be chalazion, hordeolum, pimples, blackheads, or styes.

The above overviews are intended to illustrate exemplary embodiments which will be best understood in conjunction with the detailed description to follow, and are not intended to limit the scope or meaning of the appended claims. Those skilled in the art will appreciate the scope of the present invention and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the invention, and together with the description serve to explain the principles of the invention. Certain illustrative embodiments illustrating organization and method of operation, together with objects and advantages may be best understood by the detailed description that follows taken in conjunction with the accompanying drawings in which.

DETAILED DESCRIPTION OF THE PREFERRED EMBODIMENTS

Figure 1:
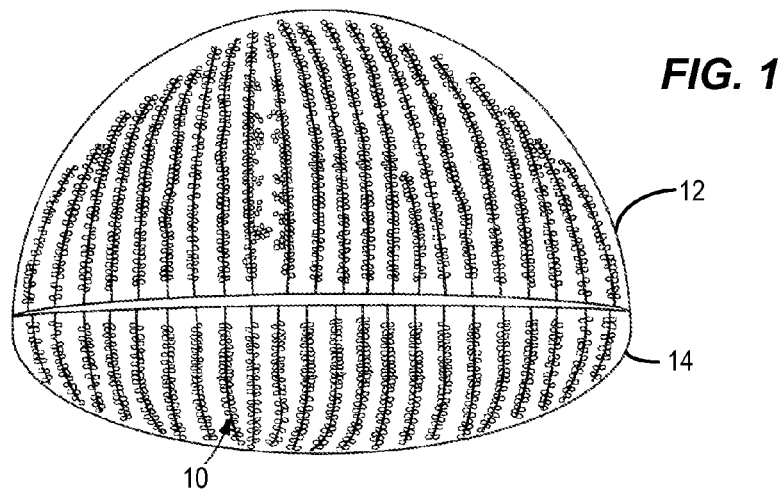
FIG. 1 depicts upper and lower human eyelids showing the meibomian glands.

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims. While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality," as used herein, is defined as two or more than two. The term "another," as used herein, is defined as at least a second or more. The terms "including" and/or "having", as used herein, are defined as comprising (i.e., open language). The term "coupled," as used herein, is defined as connected, although not necessarily directly, and not necessarily mechanically.

Reference throughout this document to "one embodiment," "certain embodiments," "an embodiment," or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B, or C" means "any of the following: A; B; C; A and B; A and C; B and C; A, B and C." An exception to this definition will occur only when a combination of elements, functions, steps or acts are in some way inherently mutually exclusive.

As used herein, the term "melt" and variants thereof are to be interpreted broadly to encompass changing the form or state of the obstructive material causing or contributing to an obstruction related to a disorder of the eye or eyelid structure to less of a solid form from a previously existing state or form or changing to more of a liquefied or gaseous state or form from a previously existing state or form causing the obstruction, including but not limited to dissolving, loosening, liquefying, and/or softening of the obstructive material to be removed, or dissolving loosening, liquefying, or softening of material that holds together particulate matters causing or contributing towards the obstruction related to a disorder of the eye or eyelid structure and other modalities.

As noted above, meibomian gland dysfunction (MGD) is one example of an obstructive disorder that is known to be a major cause of dry eye syndrome. The disorder is characterized by a blockage of some sort within the meibomian glands preventing normal lipid secretions from flowing through the orifices and out of the glands to the tear film. Obstructions or occlusions of the meibomian glands may be present at the orifice of the gland, the main channel of the gland, or possibly in other locations including the main channel of the gland which may be narrowed or blocked. It has been theorized that the acini of the glands may have valves at their junction with the main channel of the gland, and that these valves may be obstructed in some instances leading to reduced or blocked flow from the acini. These obstructions or occlusions may have various compositions.

Figure 2:
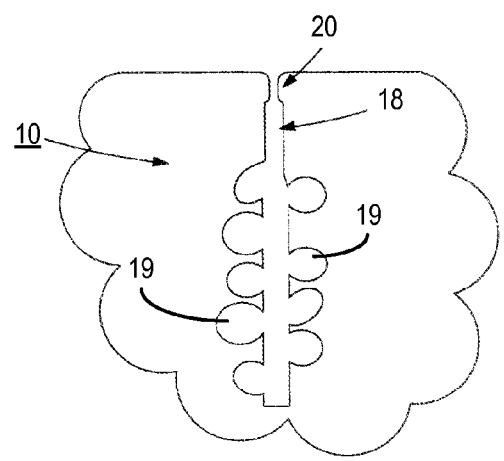
FIG. 2 is a cutaway view of an illustrative meibomian gland 20.

To facilitate an example disorder to which the present invention can be used to treat, MGD is discussed. Referring now to FIG. 1, the location of the meibomian glands 10 are shown on the upper and lower eyelids 12 and 14 respectively. As briefly stated herein above, the upper lid contains about 25 meibomian glands and the lower lid contains about 20 meibomian glands, with significant variation. As shown in cross-sectional view of one gland 10 in FIG. 2, each gland includes a central duct or channel 18 into which the secretion flows from acini 19 and an orifice 20 which opens on to the eyelid margin and through which the secretion flows in order to be added to the tear film upon blinking. It will be seen that the glands are of different size, depending upon the location in the eyelid and that the orifice 20 is narrower than the central duct 18.

Figure 3:
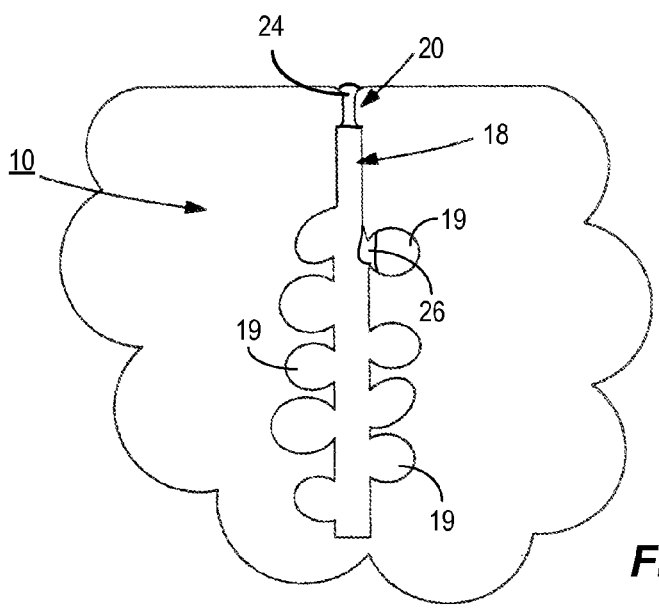
FIG. 3 is a cutaway view of meibomian gland 20 illustrating several obstructed areas.

Obstruction composition will vary with the etiology which produced it. However, the obstruction will, in most cases observed to the present, be a combination of dead cells, bacteria, desquamated cells and desquamated cells aggregating in keratotic clusters, milky fluid, inspissated or creamy secretions, or any combination of the foregoing in solid, semi-solid, and thickened forms. Referring to FIG. 3, a simplified view of exemplary obstructions to gland 10 are depicted. In this example, which is by no means necessarily representative of all meibomian gland obstructions, as explained above, a solid or semi-solid or thickened plug 24 is depicted which is fully occluding the orifice 20 of gland 10. Another obstruction 26 is shown at a junction from one of the acini 19 with the central duct. As previously noted, this may be the site of a valve in the gland structure, but embodiments consistent with the present invention should not be limited by theories of the actual meibomian gland structure.

As noted previously, other obstructive disorders of the eye and/or eyelid are also problematic for those afflicted with such disorders. Examples include chalazion, hordeolum, pimples, blackheads, styes and other disorders characterized by obstruction of a gland or other passage or opening of the eye or eyelid structures. In the case of chalazion, the disorder is the result of blockage of a gland such as the meibomian gland (also known as a meibomian gland lipogranuloma) which swells to produce a lump on the eyelid. A hordeolum or stye is a localized infection or inflammation of the eyelid margin involving hair follicles of the eyelashes (i.e., an external hordeolum) or meibomian glands (i.e., internal hordeolum). Pimples are blockages of the pores of the skin, while a blackhead (medically known as an open comedo) is a yellowish or blackish bump or plug on the skin. A blackhead is a type of acne caused by excess oils that have accumulated in the sebaceous gland duct and are often caused by excessive oil and makeup. Each of these disorders are characterized by obstruction of a gland or other passage or opening of the eye or eyelid structures. Other disorders that can be similarly characterized by an inhibition, obstruction, or other interference with the proper flow of fluids or by having an obstruction that can be melted or be related to a fluid whose flow characteristics can be improved may benefit from the treatments disclosed herein.

A number of treatment techniques have been proposed to restore meibomian glands to normal functionality, but it has been determined that heat is beneficial in treating MGD. Upon further investigation, these techniques also appear beneficial in the treatment of other obstructive disorders such as chalazion, hordeolum, pimples, blackheads, styes and other disorders characterized by obstruction of a gland or other passage or opening of the eye or eyelid structures. Depending upon the nature of the obstruction, heat may be beneficial in actually melting or loosening the obstructing material or material binding solid particles to form the obstruction and increasing the viscosity of the fluid, thereby permitting the fluids to flow more freely. While the heat treatment methods described in the Background section hereof have been found to have many drawbacks, the heating techniques described in the above referenced copending applications have been found effective and beneficial. Generally speaking, these devices produce a regulated heating of the eyelid (as measured at the outer surface thereof) by direct contact with the eyelids to a therapeutic temperature of greater than 37 degrees Celsius, and more preferably between about 42 and 47 degrees Celsius with a target temperature of 45 degrees Celsius. However, other devices may be used which are placed proximate to the eyelids to provide the desired heat.

The outside skin surface of the human eyelid has been observed to be approximately 1-2 degrees Celsius cooler than body temperature, with some variation. Increasing the temperature to at least 37 degrees Celsius can begin to provide therapeutic effect for milder cases of obstructive disorders of the eye and/or eyelid. One preferred range for treatment is 42 to 47 degrees Celsius, with a target of 45 degrees Celsius has been found effective and comfortable to the patient. In certain embodiments, the mechanical or other energy form treating is carried out during or immediately after the end of the time period, and preferably with a heated instrument so as to maintain the more fluid state of the obstruction. Energy treatment can be carried out by any mechanism that induces mechanical or other pressures, including but not limited to vibratory, milking, pulsing pressure, squeezing and other actions to express fluids from the obstructed structure and/or dilate the duct, opening or orifice of the affected structure. The energy can take any form that applies pressure on the affected structure to assist in pushing the blockage or obstruction out of the affected structure while the obstruction is softened by heat. Even higher temperatures (e.g., 50-55 degrees Celsius) can be used (or pulsed for short periods), especially if the eyelid has been anesthetized, in which case much hotter treatment for shorter time can be used without permanent injury to the patient. Generally, higher temperatures can be used for shorter periods of time. Moreover, the temperature and time used should be individualized based on the severity of the condition and the tolerance of the patient. It has been found that lighter skinned patients can generally tolerate less heat than darker skinned patients, and darker skinned patients tend to exhibit less inflammation as a result of exposure to the heat. Treatment times and/or temperature can be adjusted to account for these differences. Each of the above temperatures refers to the temperature as measured at the outer surface of the eyelid.

Also, in certain embodiments, the patient is more comfortable when the treatment begins at a lower temperature and the temperature is raised over time. Hence, the temperature should be regulated, where regulation should be interpreted to mean that the actual temperature applied at the outer surface of the eyelid is controlled or regulated in a manner that is repeatable. The temperature profile for heat application may be a constant temperature, or may have ramp-ups, ramp-downs, peaks, valleys, can be pulsed, or can be modulated with various characteristics, etc., but such profile should be regulated so as to be repeatable. It has also been found that modulating the temperature can result in a higher average temperature than a constant temperature, and may be useful in some applications.

This temperature can be maintained at a therapeutic temperature for a treatment period of approximately 1-60 minutes (or even beyond have been found safe and useful for some patients). Either during or after such treatment by controlled heat, expression of fluids from the affected structures has been found to clear obstructions which have essentially melted or been placed in a suspension state (by virtue of melting materials binding solids together). The above applications disclose devices which generally apply a milking action to the eyelid to express the fluids or suspensions or to otherwise stimulate the movement of fluids from the meibomian glands—such fluid now including melted or suspended materials causing the obstructions or occlusions. However, it has been noted that similar treatments can be applied to facilitate drainage of other structures exhibiting obstructive disorders of the eyes and/or eyelids. In some instances, just gentle continuous force applied to the eyelid will assist in expression of the fluids and suspensions, while in others vibration can be used simultaneously or immediately after the heating. For purposes of this document, the term "melted" is to be interpreted to be inclusive of states in which solid particles remain suspended within a liquid fluid.

In certain embodiments, such devices that apply regulated heating of the eyelids are disclosed in previously referenced U.S. patent application Ser. No. 11/434,054, filed May 15, 2006 and entitled "Method and Apparatus for Treating Meibomian Gland Dysfunction" to Korb et al., Ser. No. 11/434,033, filed May 15, 2006 entitled "Melting Meibomian Gland Obstructions," to Grenon et al., 60/880,850, filed Jan. 17, 2007, Ser. No. 11/541,418, filed Sep. 29, 2006 entitled "Treatment of Meibomian Glands," to Korb et al., Ser. No. 11/434,446, filed May 15, 2006 entitled "Method and Apparatus for Treating Gland Dysfunction," to Korb et al., Ser. No. 11/541,308, filed Sep. 29, 2006 entitled "Melting Meibomian Gland Dysfunctions" to Grenon et al., and 60/700,233, filed Jul. 18, 2005 entitled "Method and Apparatus for Treating Gland Dysfunction," all of which are hereby incorporated herein by reference in their entireties. In certain embodiments, these devices utilize a heater unit having a heating element that produces heat when an electrical signal is applied thereto. A temperature regulator applies the electrical signal to the heating element in order to achieve heating of the heating element to a specified temperature range. An eyelid interfacing mechanism couples the heater unit to the eyelid to achieve regulated heating of the eyelid within the specified temperature range.

Such a device provides regulated heating to a therapeutic temperature. Conventional hot compresses and the IR heating mechanisms described above background do not provide regulated controlled heating at a therapeutic temperature and are less effective than the regulated heat applied using the devices described in the above-referenced patent applications that are incorporated herein.

In another embodiment disclosed in these patent applications, an apparatus that provides controlled heat to at least one of a patient's eyelids has a heater unit, and the heater unit having: a heating element having first and second surfaces that produces heat when an electrical signal is applied thereto; a thermal heat sink, coupled to the first surface of the heating element in order to transfer heat from the heating element to the eyelid; an insulator coupled to the second surface of the heating element in order to reduce heat loss from the second surface; and a back plate that couples to the insulator. A temperature regulator applies the electrical signal to the heating element in order to achieve heating of the heating elements to a specified temperature range. Goggles suitable for attaching to the patient's head and covering the eyelid of the patient with a lenspiece are provided with the lenspiece having a threaded aperture therein. A threaded shaft passes through the threaded lenspiece and coupled to the heater unit at the back plate so that the heater unit can be moved into contact with the eyelid by screwing the shaft into the aperture until contact with the eyelid is achieved.

Many devices can be used to generate heating of the affected structures in accordance with embodiments consistent with the present invention. By way of example and not limitation, in one form of this device as described in the above-referenced U.S. Provisional Patent Application Ser. No. 60/880,850, a lenspiece/insulator is provided which is concave in shape on the eyeball side and mirrors the curvature of the eyeball, substantially similar to a contact lens. As employed herein, the term "insulator" is intended to include any component or material wherein there is greater resistance to thermal conduction or radiation towards the surface of the eye than towards the eyelid. Stated alternatively, in the insulator thermal energy radiates more easily towards the eyelid than towards the eyeball surface in order to minimize the possibility of causing injury to the eyeball. In a model that supplied heating alone, the diameter was sufficient to more than cover the cornea or in the approximate range of 15 mm to 25 mm would be sufficient for most eyes assuming a corneal relief zone of approximately 16 mm. It will be noted however, that the diameter of the insulator can vary beyond the ranges stated above. Further, the insulator is constructed from a biocompatible material such as polymethylmethacrylate (PMMA) or in the case of the prototype that was constructed, epoxy or other materials well known to those skilled in the art. The insulator may be flexible, but ideally should be only minimally compressible, as will become clear from the discussion that follows.

According to certain embodiments consistent with the invention, the lenspiece insulator is inserted on the surface of the eye, behind the rear surface of the eyelid and should include smooth edges so as not to scratch or cut either the eyelid or the eye. As used herein the term "eyelid" or "eyelids" is intended to include the upper lid and the lower lid, either singly or in combination. The insulator provides a back plate against which pressure may be applied. In limited circumstances when the obstructive disorder is minimal the obstruction may be cleared merely through the application of pressure externally applied to the eyelid, such as gentle finger pressure. More specifically, with the insulator in place behind the eyelid, finger pressure is applied to the external surface of the eyelid, the eyelid being sandwiched between the finger and the insulator.

In other instances, the obstruction may be blocked to a degree greater than can be treated with simple pressure alone. In such thermal energy is applied to the eyelid in order to loosen, break up, fracture, soften or liquefy at least a portion of the occlusion. Thermal energy may be applied by any one of the well known means for applying thermal energy such as modalities such as resistive, IR (infrared), ultrasonic heating, microwave, any one of the numerous "hot pads" that chemically produce an exothermic reaction or in the simplest form a hot compress. In the present embodiment, at least a portion of the heat may be provided by resistive heating elements or by the excess heat generated in LEDs. Experimentation has revealed that in order to be clinically effective the eyelid should be heated to a temperature of between about 35 degrees Celsius and 47 degrees Celsius. The length of time for which thermal energy, i.e., heat is applied to the eyelid depends upon the extent of the obstruction as well as the composition of the obstruction. In very minor cases, heat may be applied to the eyelid for less than three minutes or even as little as five to fifteen seconds. On the other hand, extreme blockage may require as much as thirty minutes of heating to soften the obstruction prior to the application of pressure to the eyelid to express the softened obstruction. Experimentation has further revealed that the eyelids are efficient heat exchangers with circulating blood acting as the cooling mechanism and that the eyelid temperature returns to normal in less than two minutes at which time the obstruction re-hardens, making extraction difficult. It is therefore necessary to apply the aforesaid expressive force to the eyelid within that time frame in order for the treatment to be successful. Thus, gentle finger pressure to urge the obstruction from the obstructed structure can be employed. Again, depending on the nature and location of the obstruction, mere compressive force may be effective in some instances.

In a further embodiment, the insulator is inserted between the rear of the eyelid on the surface of the eyeball as previously described. An eyecup is employed to provide external pressure to the eyelid against the insulator. In one embodiment, thermal energy is applied as described above, an eyecup (which may be unheated) is placed on the outer surfaces of the eyelid and pressure is applied thereto to express the softened obstruction. The eyecup mirrors the size and shape of the eyelids when closed.

The eyecup is adapted to overlie the outer surface of the eyelid, substantially conforms to the surface shape thereof and is adapted to cooperate with the lenspiece insulator. The eyecup includes a centrally located longitudinal slot which receives the male connector member. In certain embodiments, positioned on the underside of the eyecup is a diaphragm arrangement as described in U.S. Provisional Application Ser. No. 60/880,850. The pair of diaphragms are in fluid communication with each other and include an inlet or inlet. The diaphragms are attached to the eyecup via conventional means such as glue. It will be noted that the eyecup could be provided with a single diaphragm with a hole defining an opening through which the male connector member may pass.

The diaphragms may be fabricated from a biocompatible material such as polyurethane foam (open or closed cell), a sealed air balloon, and/or a gel-filled bladder. Again, depending upon the type and degree of obstruction, the diaphragms will vary in thickness and/or durometer. In an alternate embodiment, diaphragms may comprise bladders which may be fabricated from any flexible expandable material such as rubber or plastic, however, it is preferred that the coefficient of expansion be linear with respect to the amount of fluid added. The bladders may be partially filled with a constant amount of fluid or they may be provided with a rudimentary pump connected to an inlet such as is used with a perfume aerosolizer. The fluid is preferably air, but may also be a liquid such as water, saline, etc. Further, while not shown, the fluid may also be heated in order to assist in the softening of any obstructions which may be present. It will be noted that for any given patient, either or both of the insulator and fluid may be heated in order to soften an obstruction in an affected structure. The bladders could be fabricated in such a manner that as they inflate pressure is applied which urges the softened gland obstructive material up the gland channel and out of the gland orifice to clear the gland. One method would be to increase the thickness of the bladders such that there is less resistance (less thickness) to inflation near the bottom of the gland and the resistance increases (greater thickness) as one reaches the gland orifice.

In operation, the lenspiece insulator is placed on the sclera of the eye in much the same manner as a contact lens is inserted. The eyecup and bladder are then positioned with the concavity facing the eyelid. The connector is then used to couple the lenspiece insulator to the eyecup. Heat is then activated by a switch or control processor or other means to which the heated fluid in the bladders may be added simultaneously or serially for the preselected period of time, for example, two minutes. Thereafter, or simultaneously with the application of heat, the bladders may be expanded which will urge the softened obstructive matter and force it out of the affected structure, thus unblocking the effected structure. When treatment is complete, the connector is disengaged and the lenspiece insulator and bladders are removed. The assembly can then be readily removed from the eyeball and treatment in some instances is complete. In other instances, further treatment with pharmaceutical agents can be used to either enhance further fluid drainage, reduce inflammation, clear or prevent infection or other modalities depending upon the affliction and structure being treated.

It will be noted that various mechanisms to lock the insulator to the eyecup could be employed such as a ratchet type mechanism and a press fit, as well as other mechanisms well known to those skilled in the art, not discussed herein. While not specifically required, it is preferable that the locking mechanisms be near "zero insertion" force in order to minimize the potential for eye injury.

While the above-described structure can be used for effecting the heating and application of pressure to drain fluid from the effected structure, other devices could also be used without limitation.

Many variations in these embodiments are possible including, but not limited to, providing a sensor that senses temperature and provides temperature information to the temperature regulator. In certain embodiments, the eyelid interfacing mechanism may comprise goggles that are adjustably coupled to the heater unit in order to move the heater unit to achieve contact with the eyelid, such as described in previously referenced U.S. patent application Ser. No. 11/541,291. The goggles may be adjustably coupled to the heater unit by a threaded connection so that a position of the heater unit can be adjusted by a threading action. In certain embodiments, the heater unit may have a thermal heat sink, coupled to a surface of the heating element in order to transfer heat from the heating element to the eyelid, such as described in previously referenced U.S. patent application Ser. No. 11/541,308. The thermal heat sink may be, for example, at least one of a thermally conductive rubber member, a thermally conductive silicon member, an encapsulated fluid containing member, and a solid conductive member. A thermally conductive gel, cream, or liquid can be placed between the heat sink and the eyelid to enhance thermal conduction from the thermal heat sink to the eyelid.

In certain embodiments, the heater unit may have an insulator coupled to a surface of the heating element in order to reduce heat loss from the heating unit in a direction other than a direction toward the eyelid. The thermal insulator may be one of a non-thermally conductive foam element, a non-thermally conductive rubber element, and a non-thermally conductive solid element in certain embodiments. The temperature regulator may apply a pulse width modulated electrical signal to the heating element in order to regulate the heat produced thereby, and the pulse width modulated electrical signal may be produced under control of the control processor.

In certain embodiments, the temperature regulator may incorporate a switch that selectively applies the electrical signal to the heating element in order to regulate the heat produced thereby. The electrical signal may be at least one of a current and a voltage that is selectively applied to the heating element under control of the control processor. The heater unit may have a flexible portion that contacts the eyelid in order to conform to the eyelid or may have a rigid portion that contacts the eyelid, and wherein the rigid portion is shaped to conform to the shape of the eyelid, or a combination thereof. The heater unit may have an adhesive for attaching the heater unit directly to the eyelid or may be attached to the eyelid by use of adhesive tape.

In certain embodiments, a user interface permits a user to establish at least one of a time and a temperature for the treatment. In certain embodiments, a vibration generator generates vibration of the eyelid to stimulate secretion from the meibomian glands, wherein the vibration generator may impart mechanical or other forms of energy to the eyelid having both an amplitude and frequency.

These and other heating and/or pressure inducing devices for facilitating the melting and expression of obstructions in the eye, eyelids, or other related structures are disclosed in the above-referenced patent applications, and are incorporated herein by reference in their entireties.

Hence, in view of the above, either immediately after treatment with heat, or during such heat treatment, mechanical or other forms of treatment using, for example, constant force, squeezing (e.g., by manual expression or otherwise), milking action or vibration can be applied to the eyelid to stimulate clearing of the fluids or suspensions from the obstructed structure. If treatment is carried out after heat treatment, it should be carried out immediately thereafter while the obstructive material of the meibomian gland is in a melted state.

Figure 4:
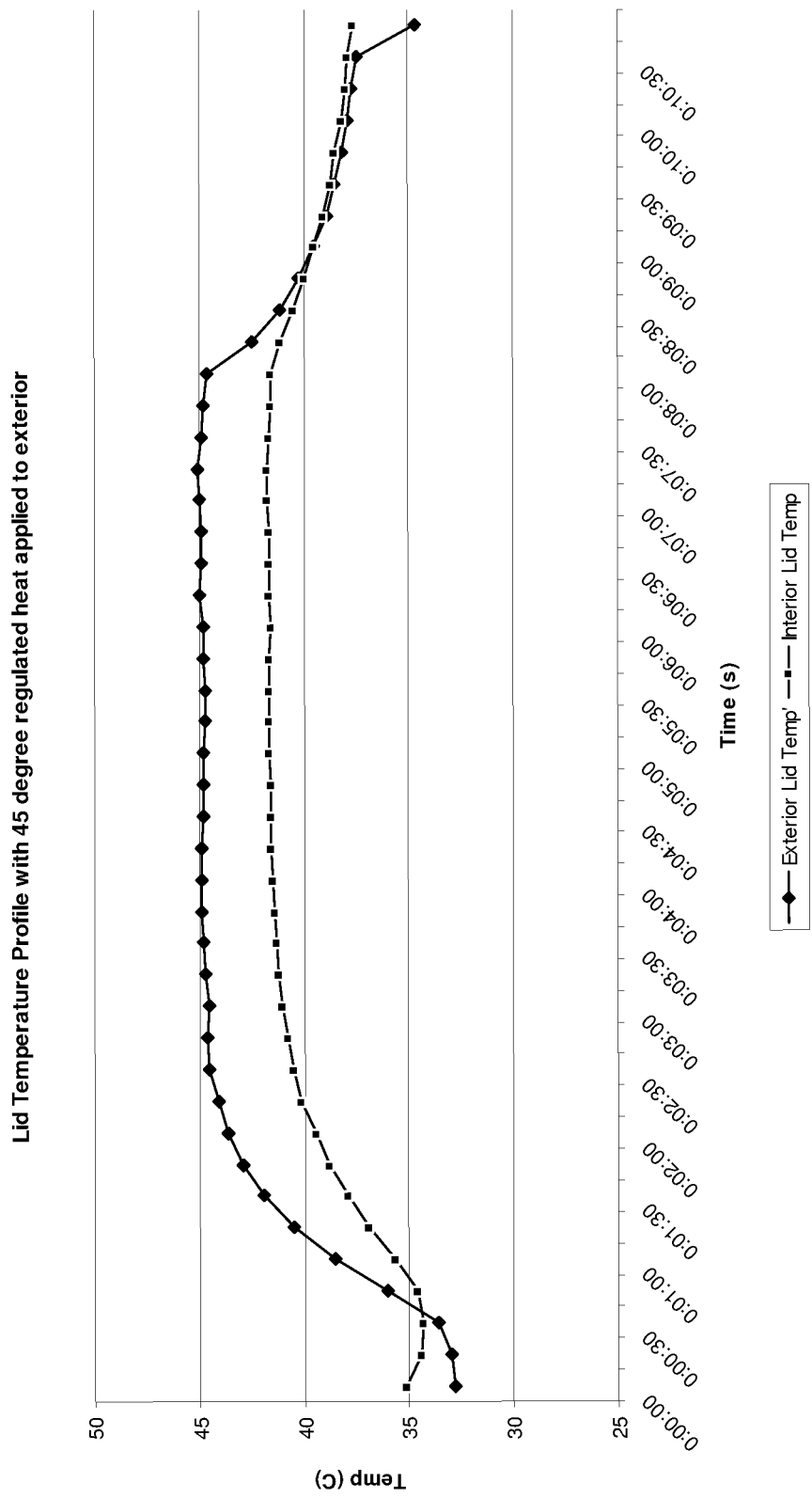
FIG. 4 is a graph of inner and outer surface temperatures of a patient's eyelid while the outer surface of the eyelid is heated to about 45 degrees Celsius.

Referring now to FIG. 4, a graph depicts the inner surface of an eyelid and an outer surface of an eyelid when a source of constant heat at about 45 degrees Celsius was applied to an example subject patient. It should be noted that the circulatory system attempts to regulate the temperature of the eyelid, and blood flow increases with the application of heat. For this patient, it took approximately 4 minutes for the eyelid's outer surface to reach about 45 degrees Celsius, and the inner surface of the eyelid never reached this temperature—presumably because of the body's heat regulatory mechanisms. Hence, if a 45 degree Celsius constant heat source is used, it may take at least about 4 minutes to stabilize eyelid temperature and reach a therapeutic temperature.

It is also noted from this graph, that when the heat source is removed from the eyelid, the temperature drops very quickly to body temperature. In virtually all cases, this temperature will drop within 2-3 minutes, but more commonly, only about 30 seconds to 90 seconds are required for the patient's eyelid temperature to drop. In this example, the temperature dropped very quickly over the first thirty seconds after removal of the heat. During this short time period, some or all of the melted obstruction may re-solidify. Hence, if manual expression techniques are to be carried out subsequent to application of heat, the manual expression should follow immediately, or within about 90 seconds—with shorter intervals being preferred, e.g., within 30 seconds, or in any event, prior to reversal of the effects of the application of the regulated heat source such that at least a portion of the occlusion is removed. It will thus be clear from this graph that prior techniques of using warm compresses may be substantially less effective if manual expression does not follow within an extremely short period of time. Moreover, if the compresses cool below a therapeutic level prior to manual expression, they may provide minimal benefit to a patient suffering from substantial obstruction.

It has been discovered that the problem with most pharmacological treatment modalities for dry eye syndrome is that the pharmacological agent is unable to affect MGD when the disorder involves obstructions of the gland. That is, the currently known pharmaceutical treatments simply cannot unclog the meibomian glands to permit flow of lipids. While antibiotic treatment, steroid treatment, or other pharmacological treatments may be useful for other causes of dry eye, they have been found ineffective (or at most, to provide temporary symptomatic relief) when obstruction of the meibomian glands is involved. Similar logic can be applied to other obstructive disorders of the eye and/or eyelid. Until the actual obstruction is removed, the flow of fluids—whether naturally produced fluids as in the case of the meibomian glands, or other fluids generated as a result of infection or blockage such as pus, treatments which promote lipid production or fluid flow per se cannot generally relieve the problem until the blockage is removed so that fluid flow or drainage actually occur. In fact, promoting lipid production may cause more meibomian difficulties and inflammation of the glands. Once this point is reached, however, pharmacological agents that either promote fluid flow or infection healing can be beneficial.

Other pharmacological agents may assist in promoting tear production or otherwise assisting in the lubricating function of the eye by promoting an improvement in the tear film. Used alone, such treatments may be ineffective or only partially effective, whereas, used after clearing of the meibomian glands, tear ducts or other structures may restore normal or near normal production of all components of the tear film. Hence, many pharmacological agents may be appropriate for further enhancement of the tear film and may be extremely beneficial once the eyes are returned to more normal function.

Figure 5:
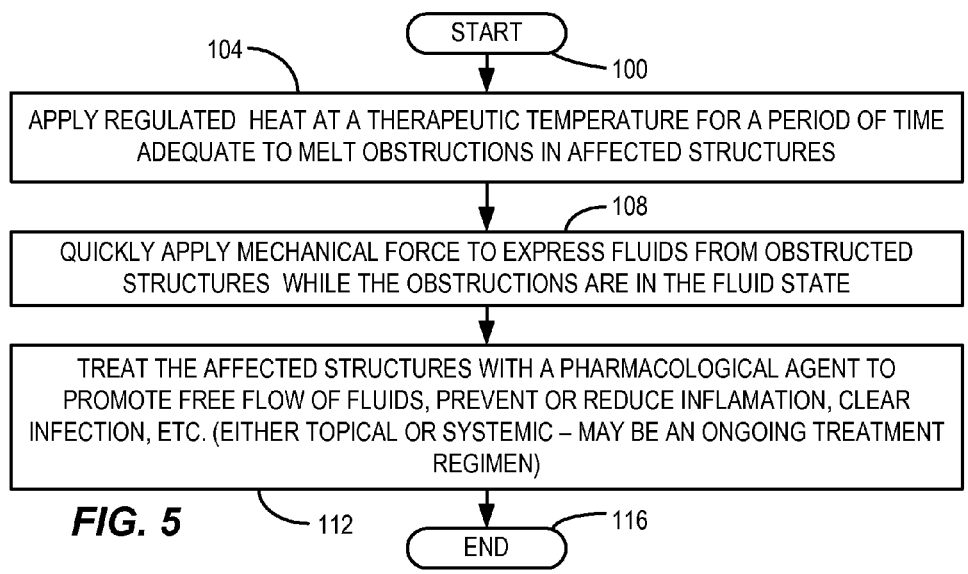
FIG. 5 is a flow chart depicting a treatment process consistent with certain embodiments of the present invention.

Hence, with reference to FIG. 5, a treatment regimen is described starting at 100, after which a controlled heat such as produced by the various apparatus described in the above-referenced and incorporated by reference patent applications is applied to the eyelids at 104. The preferred heat is greater than 37 degrees Celsius, with a preferred range of heat between approximately 42-47 degrees Celsius, with a target of 45 degrees Celsius. However, greater temperatures Celsius for shorter periods of time will provide therapeutic benefit, with the possible side effect of minor skin burns that do not cause lasting damage. Below this temperature range, treatment tends to be less effective or ineffective. Temperatures above this range can cause substantial patient discomfort, injury to the eyelids and possibly the eye. At higher temperatures within the range, the patient may find the heat to be somewhat uncomfortable, but the treatment time can be reduced and the discomfort can be moderated with anesthetic. Lower temperatures in the range are effective but generally take a longer heating period.

As a rule of thumb starting point, fifteen minutes at a relatively constant 45 degrees Celsius generally works well for many patients with mild to moderate obstructive disorders without undue patient discomfort. Time ranges from about 1-60 minutes or even beyond may be used depending upon the type and severity of the condition, the temperature, anesthetic used, and patient tolerance. In experiments, times beyond one hour were used without apparent adverse effects.

Once the heat treatment is completed (and/or during the heat treatment), mechanical or other force can be applied (step 108) in any of the above modalities discussed to express the fluids or suspensions from the effected structures while the obstructions are in the melted state. When expression is used, it is preferable that any instrument used in the expression process be heated so as to simultaneously apply or assist in maintaining heat to the affected structure at the time of expression.

While manual expression of the obstructed structure can be painful and is invasive with inconsistent results when used alone due to variations in manual control and/or manipulation, and while this method of treating obstructed structures can also be quite uncomfortable to the patient because it requires the physician to squeeze the structure, this technique may prove useful as a step in the process used selectively in difficult cases. As noted, the heat treatment described may be beneficial in combination with automated expression devices to assist in clearing obstructed structures to enhance the normal flow of fluids. After heat treatment, the expression of secretions from an obstructed structure is generally dramatically more effective with less patient discomfort and better results than no heat treatment. As noted previously, when expression of the obstructed structure is used, it is preferable that any instrument used in the expression process be heated so as to simultaneously apply heat or assist in maintaining heat to the structure at the time of expression.

Once the occlusions and other foreign substances have been cleared from the structure (steps 104, 108), treatment with any of a variety of pharmacological agents, either topical or systemic) in order to minimize inflammation of the structure, clear infections, prevent further blockages, thin the lipids, promote production of tears, enhance the composition of the tear film, or any other pharmacological modality that promotes the free flow of fluids, healing or enhanced lubrication of the eye (step 112). Pharmacological treatment may be carried out either for a short duration (e.g., to clear an infection or inflammatory condition), or for ongoing therapy (e.g., as in pharmacological agents that thin the lipids, reduce inflammation or treat other modalities of dry eye syndrome). This process ends (step 116).

Many pharmacological agents have been proposed for treatment of dry eye syndrome, any of which may be effective or more effective upon clearing of obstructions within the meibomian glands. Some of these agents may also be effective in treatment of other obstructive disorders such as those listed above as examples. Some of the pharmacological agents that may be utilized include, but are not limited to: anti-inflammatory agents, antibiotics such as topical or oral tetracycline and chemically modified tetracycline, testosterone, topical or oral corticosteroids, topical androgens or androgen analogues, omega 3 fatty acid compounds such as fish oils, laennec, enzymes that promote lipid production, agents that stimulate production of enzymes that promote lipid production, and any agent which acts as a secretagogue to enhance meibomian gland secretion or secretion of other tear components. Androgen and androgen analogues and TGF-β have been reported to act as a secretagogue to enhance meibomian gland secretion, agents that replace or promote production of any tear component, and there are likely many others. These compounds are illustrative examples of appropriate pharmacological agents, but those skilled in the art will appreciate that other pharmacological compounds may be utilized upon consideration of the present teachings. It is further noted that multiple modalities may be involved in causing dry eye syndrome, but treatment of only one modality may not result in full resolution. Hence, the restoration of normal or near normal lipid flow from the meibomian glands may be only a part of the solution—with pharmacological treatment of the other modality or modalities of the disease restoring a normal tear film. However, when significant MG dysfunction is involved, treatment of the other modalities alone is likely to be less than satisfactory. In the case of other obstructive disorders, some of the same pharmacological agents may similarly be effective, including anti-inflammatory, antibiotic, and steroidal agents.

A variation of the above treatment is described in connection with FIG. 6 starting at step 130, after which a controlled heat such as produced by the various apparatus described in the above-referenced and incorporated by reference patent applications is applied to the eyelids (step 104) as in the prior treatment method. The preferred range of such heat is again between approximately 42-47 degrees Celsius, with a target of 45 degrees Celsius. Again, time ranges from about 1 to 60 minutes and beyond may be used, depending upon severity of the condition, the treatment temperature, and patient tolerance.

In this embodiment, during the heat treatment, mechanical or other force can be applied (step 138) in any of the above mechanical or other modalities discussed, including those referenced and incorporated by reference, to express the fluids or suspensions from the meibomian glands while the obstructions are in a liquid or suspension state during application of the heat.

Depending upon the patient response to heat in combination with simultaneous mechanical or other force (step 138), additional force can be applied immediately subsequent to removal of the heat (step 142). In this case, it is also preferred that heat be maintained during the time of expression or force being applied as described. That is, it is preferred that any probe or other instrument used during the expression be heated to help maintain the obstruction in a liquid or suspension state. Such force can be manually applied by squeezing the eyelids at appropriate locations where obstructions appear to remain, or automated mechanical means or other means may be employed if available.

Once the occlusions and foreign substances have been cleared from some or all of the affected structures (steps 104, 138, 142), the structures can be treated with any of a variety of pharmacological agents (either topical or systemic) in order to minimize inflammation, clear infections, prevent further blockages, thin the lipids, or any other pharmacological modality that promotes the free flow of the fluids, promote healing, reduce inflammation or otherwise promote an improved tear film or reduce discomfort (step 112) as before. As noted, pharmacological treatment may be carried out either for a short duration (e.g., to clear an infection or inflammatory condition), or for ongoing therapy (e.g., as in pharmacological agents that thin the lipids, improve the tear composition, or reduce inflammation). This process ends (step 150).

Figure 6:
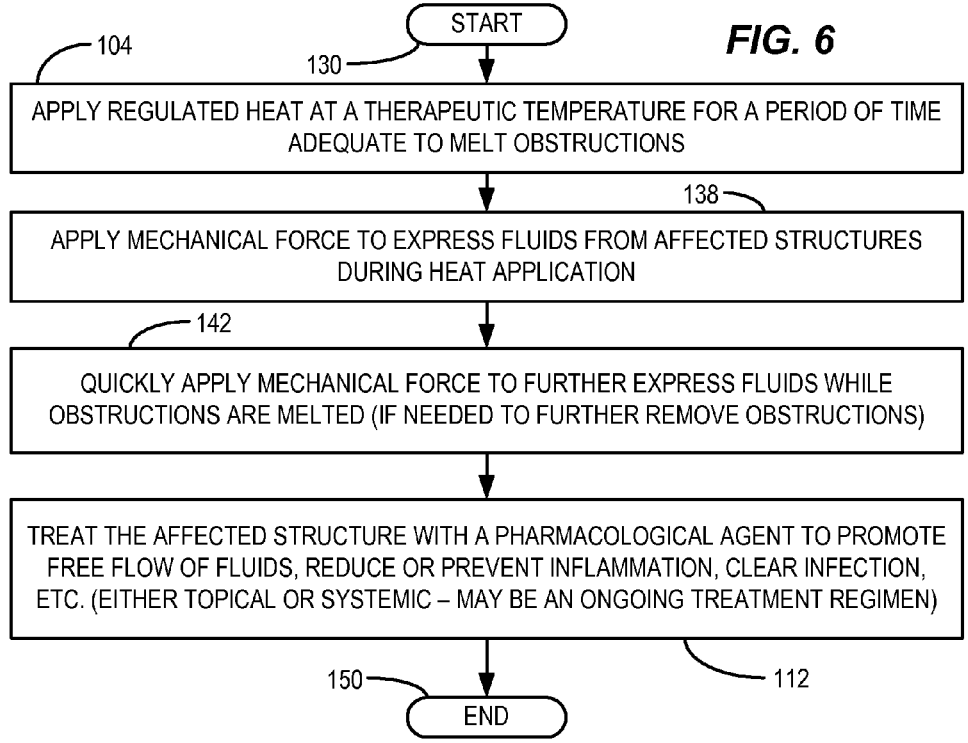
FIG. 6 is a flow chart depicting another treatment process consistent with certain embodiments of the present invention.

The above processes, whether involving the process of FIG. 5 or FIG. 6, may be repeated or interchanged at time intervals as needed to create or maintain proper flow from or healing of effected structures. Such treatments, or portions thereof, may need to be periodically repeated for some patients in order to maintain proper function of the structures that are being treated for obstruction.

Thus, in accordance with certain embodiments consistent with the present invention, a method of treating mammalian eye or eyelid structures involves clearing the structures by applying a regulated heat to an eyelid to reach a temperature adequate to melt obstructions in the effected structure and maintaining the heat for a time period adequate to melt the obstructions and place the obstructions in a fluid or suspension (melted) state. The effected structures can then be treated to express fluid or suspension, wherein the treatment is carried out either during the time period or after the time period but while the obstruction remains in the melted state. The process may be enhanced by a heated treatment device for applying the force to maintain the temperature and the melted state of the obstructive material. Subsequent pharmacological treatment of the structure by use a pharmacological agent (topical or systemic) can then be used to assist in healing or maintaining proper flow of fluids.

In accordance with certain embodiments, the time period can be approximately 1 to 60 minutes, and approximately 15 minutes is generally suitable for mild to moderate cases. The temperature should be greater than 37 degrees Celsius and the preferred range is approximately 42 to 47 degrees Celsius with a target of 45 degrees Celsius at the eyelid's outer surface has been found effective and comfortable to the patient. In certain embodiments, the treating is carried out as soon as possible after the heating, and preferably within about 30-90 seconds, so that the obstruction will remain in a melted state during the expression process. In other embodiments, the treatment is carried out by at least one of application of constant pressure, squeezing, milkingly expressing the fluid or suspension from one or more of the glands while simultaneously applying heat, or applying vibratory stimulation to the eyelid while simultaneously applying heat. Many variations and alternative embodiments will occur to those skilled in the art upon consideration of the present teaching.

Those skilled in the art will recognize improvements and modifications to the preferred embodiments of the present invention. All such improvements and modifications are considered within the scope of the concepts disclosed herein and the claims that follow.

What is claimed is:

1. A method of treating obstructive disorders of a meibomian gland channel of an eyelid, comprising:
   applying regulated heat to a channel of a meibomian gland of an eyelid containing the obstructive disorder that reaches a temperature to melt at least one obstruction in the channel and place the at least one obstruction in a melted state;
   maintaining the heat for a time period to melt the at least one obstruction and place the at least one obstruction in a melted state; and
   expressing the at least one obstruction from the channel and through an orifice of the meibomian gland by applying a milking action to the channel, wherein the expressing is carried out while the at least one obstruction is in the melted state.

2. The method according to claim 1, further comprising subsequently treating the eyelid by use of a pharmacological agent.

3. The method according to claim 1, wherein the time period comprises approximately 1 to 60 minutes.

4. The method according to claim 1, wherein the expressing is carried out using a heated instrument.

5. The method according to claim 1, wherein the temperature reaches between approximately 42 and 47 degrees Celsius.

6. The method according to claim 1, wherein the expressing is carried out within approximately 3 minutes after the end of the time period.

7. The method according to claim 1, wherein the pharmacological agent comprises at least one of a topical pharmacological agent and a systemic pharmacological agent.

8. The method according to claim 1, wherein the pharmacological agent is selected from the group consisting of anti-inflammatory agents, antibiotics, topical tetracycline, oral tetracycline, topical corticosteroids, oral corticosteroids, topical androgens, topical androgen analogues, TGF-$\beta$, omega 3 compounds, enzymes that promote lipid production, agents that stimulate production of enzymes that promote lipid production, agents that act as a secretagogue to enhance Meibomian gland secretion, and agents that replace or promote production of any tear component.

9. The method according to claim 1, further comprising repeating at least one of the applying and maintaining of regulated heat after a time interval to maintain flow of fluids from the channel and the expressing at the time interval to maintain flow of fluids from the channel.

10. The method according to claim 1, wherein the obstructive disorder comprises a disorder selected from the group consisting of chalazion, hordeolum, pimples, blackheads and styes.

11. The method of claim 1, wherein the expressing is carried out either during the time period or after the time period.

12. A method of treating obstructive disorders of a meibomian gland channel of an eyelid, comprising:
   applying a regulated heat of at least approximately 37 degrees Celsius to an eye or eyelid containing the disorder to a temperature to melt at least one obstruction in the channel and place the at least one obstruction in a melted state;
   maintaining the heat for a time period to melt the at least one obstruction and place the at least one obstructions in a melted state, and wherein the time period is between approximately 1 and 60 minutes;
   expressing the at least one obstruction from the channel and through an orifice of the meibomian gland by applying a milking action to the channel, wherein the treating is carried out while the at least one obstruction is in the melted state; and
   subsequently pharmacologically treating the eyelid by use of a pharmacological agent.

13. The method according to claim 12, wherein the temperature reaches approximately 42 to 47 degrees Celsius.

14. The method according to claim 12, wherein the expressing further comprises one or more of: applying vibratory stimulation to the eyelid, squeezing the eyelid, applying constant pressure to the eyelid, or applying pulsating pressure to the eyelid.

15. The method according to claim 12, wherein the pharmacological agent comprises at least one of a topical pharmacological agent and a systemic pharmacological agent.

16. The method according to claim 12, wherein the expressing is carried out using a heated instrument.

17. The method according to claim 12, wherein the pharmacological agent is selected from the group consisting of anti-inflammatory agents, antibiotics, topical tetracycline, oral tetracycline, topical corticosteroids, oral corticosteroids, topical androgens, topical androgen analogues, TGF-$\beta$, omega 3 compounds, enzymes that promote lipid production, agents that stimulate production of enzymes that promote lipid production, agents that act as a secretagogue to enhance Meibomian gland secretion, and agents that replace or promote production of any tear component.

18. The method according to claim 12, wherein the obstructive disorder is selected from the group consisting of chalazion, hordeolum, pimples, blackheads, and styes.

19. The method according to claim 12, wherein the expressing is carried out prior to approximately 90 seconds after expiration of the time period.

20. A method of treating obstructive disorders of a channel of an eye or eyelid including chalazion, hordeolum, pimples, blackheads, and styes, comprising:
   applying a regulated heat in the range of approximately 42 to 47 degrees Celsius to an eyelid containing the structure to a temperature to melt at least one obstruction in the channel and place the at least one obstruction in a melted state;
   maintaining the heat for a time period to melt the at least one obstruction and place the at least one obstruction in the melted state, wherein the time period is between approximately 1 and 60 minutes;
   expressing fluid or suspension from the channel and through an orifice at an end of the channel by applying a milking action to the channel, wherein the expressing is carried out either during the time period or within approximately 90 seconds following the end of the time period while the at least one obstruction is in the melted state, wherein the expressing is carried out using a heated instrument; and
   subsequently, pharmacologically treating the eye or eyelid by use of a pharmacological agent.

21. The method according to claim 20, wherein the expressing further comprises one or more of: applying mechanical energy stimulation to the eyelid, applying vibratory energy to the eyelid, squeezing the eyelid, applying constant pressure, or applying pulsating pressure to the eyelid.

22. The method according to claim 20, wherein the pharmacological agent comprises at least one of a topical pharmacological agent and a systemic pharmacological agent.

23. A method of treating obstructive disorders of a channel of the eye or eyelid including chalazion, hordeolum, pimples, blackheads, and styes in which at least one obstruction blocks flow of fluid from the channel, comprising:
applying a regulated heat source proximate to the channel for a selected time and at a selected temperature adequate to melt at least a portion of the at least one obstruction;
applying a milking action to the channel while the at least a portion of the at least one obstruction is melted such that at least a portion of the at least one obstruction is removed from the channel through an orifice at an end of the channel;
subsequently treating the disorder with a pharmacological agent.

24. The method according to claim 23, wherein the selected temperature reaches between approximately 42 and 47 degrees Celsius.

25. The method according to claim 23, wherein the pharmacological agent comprises at least one of a topical pharmacological agent and a systemic pharmacological agent.

26. The method of claim 1, wherein the applying a milking action comprises applying a regulated directional force to the channel in a direction from a bottom of the channel to a top of the channel.

27. The method of claim 12, wherein the applying a milking action comprises applying a regulated directional force to the channel in a direction from a bottom of the channel to a top of the channel.

28. The method of claim 20, wherein the applying a milking action comprises applying a regulated directional force to the channel in a direction from a bottom of the channel to a top of the channel.

29. The method of claim 23, wherein the applying a milking action comprises applying a regulated directional force to the channel in a direction from a bottom of the channel to a top of the channel.

* * * * *